United States Patent
Iyer et al.

(10) Patent No.: US 9,827,306 B2
(45) Date of Patent: Nov. 28, 2017

(54) PORCINE PARVOVIRUS 5B, METHODS OF USE AND VACCINE

(71) Applicant: Boehringer Ingelheim Vetmedica, Inc., St. Joseph, MO (US)

(72) Inventors: Arun V. Iyer, Ames, IA (US); Dianna M. Murphy Jordan, Ames, IA (US); Abby Rae Patterson, Story City, IA (US); Michael B. Roof, Ames, IA (US); Eric Martin Vaughn, Ames, IA (US); Joseph Gilbert Victoria, Ames, IA (US); Callie Ann Visek, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 0 days.

(21) Appl. No.: 14/721,490

(22) Filed: May 26, 2015

(65) Prior Publication Data
US 2015/0283230 A1    Oct. 8, 2015

Related U.S. Application Data

(62) Division of application No. 13/800,413, filed on Mar. 13, 2013, now abandoned.
(Continued)

(51) Int. Cl.
*A61K 39/23* (2006.01)
*C12N 7/00* (2006.01)
(Continued)

(52) U.S. Cl.
CPC ............ *A61K 39/23* (2013.01); *C07K 14/005* (2013.01); *C12N 7/00* (2013.01);
(Continued)

(58) Field of Classification Search
None
See application file for complete search history.

(56) References Cited

U.S. PATENT DOCUMENTS

6,228,846 B1    5/2001   Audonnet et al.
2014/0170180 A1    6/2014   Iyer et al.
(Continued)

FOREIGN PATENT DOCUMENTS

EP    0117767 A1    9/1984
WO    9803199 A1    1/1998
(Continued)

OTHER PUBLICATIONS

Mengeling et al., "The effect of porcine parvovirus and porcine reproductive and respiratory syndrome virus on porcine reproductive performance." Animal Reproduction Science, vol. 60-61, 2000, pp. 199-210.
(Continued)

*Primary Examiner* — Janet L Andres
*Assistant Examiner* — M. Franco Salvoza
(74) *Attorney, Agent, or Firm* — Marc Began; Joyce L. Morrison

(57) ABSTRACT

The present invention provides novel nucleotides sequences, protein sequences, immunogenic compositions, vaccines, and methods that relate to making and using new porcine parvovirus 5B (PPV5B) that infects, inter alia, domestic swine. The compositions and methods provide for the detection of infections by said new virus, monitoring genetic changes in the viral sequences in wild and domestic animals and herds, and making and using novel vaccines for protecting animals from infection by the virus.

6 Claims, 9 Drawing Sheets

Phylogenetic analysis of VP1/CAP region of PPV5B

Related U.S. Application Data

(60) Provisional application No. 61/765,204, filed on Feb. 15, 2013.

(51) Int. Cl.
   *C07K 14/005* (2006.01)
   *G01N 33/569* (2006.01)
   *A61K 39/00* (2006.01)

(52) U.S. Cl.
   CPC .... *G01N 33/56983* (2013.01); *A61K 2039/53* (2013.01); *C12N 2750/14321* (2013.01); *C12N 2750/14322* (2013.01); *C12N 2750/14334* (2013.01); *G01N 2333/015* (2013.01); *G01N 2469/10* (2013.01)

(56) References Cited

U.S. PATENT DOCUMENTS

| | | |
|---|---|---|
| 2014/0234354 A1 | 8/2014 | Iyer et al. |
| 2015/0246113 A1 | 9/2015 | Iyer et al. |

FOREIGN PATENT DOCUMENTS

| | | |
|---|---|---|
| WO | 9811244 A2 | 3/1998 |
| WO | 02068698 A2 | 9/2002 |
| WO | 2011063320 A2 | 5/2011 |
| WO | 2014099669 A1 | 6/2014 |
| WO | 2014127084 A1 | 8/2014 |

OTHER PUBLICATIONS

Canuti et al., "Two Novel Parvoviruses in Frugivorous New and Old World Bats". PLOS One, vol. 6, No. 12, e29140, Dec. 2011, pp. 1-9.
Cheung et al., "Identification and molecular cloning of a novel porcine parvovirus". Archives of Virology, vol. 155, 2010, pp. 801-806.
Cui et al., "Genome Sequence of Chinese Porcine Parvovirus Strain PPV2010". Journal of Virology, vol. 86, No. 4, 2012, p. 2379.
Database UniProt Accession No. K4K2G7, Jan. 9, 2013, Retrieved from EBI accession No. UNIPROT: K4K2G7, pp. 1-3.
Database UniProt Accession No. K4K4H5, Jan. 9, 2013, Retrieved from EBI accession No. UNIPROT: K4K4H5, pp. 1-3.
Duffy et al., "Rates of evolutionary change in viruses: patterns and determinants". Nature Reviews Genetics, vol. 9, 2008, pp. 267-276.
GenBank Accession No. EV964070.2, Gorodkin et al., "Porcine transcriptome analysis based on 97 non-normalized cDNA libraries and assembly of 1,021,891 expressed sequence tags". The Royal Veterinary and Bioinformatics, (IBHV) and Center for Bioinformatics, Aug. 2007, 1 page.
GenBank Accession No. EV966948.2, Gorodkin et al., "Porcine transcriptome analysis based on 97 non-normalized cDNA libraries and assembly of 1,021,891 expressed sequence tags". The Royal Veterinary and Bioinformatics, (IBHV) and Center for Bioinformatics, Aug. 2007, 1 page.
GenBank Accession No. JQ037754.1, Canuti et al., "Two Novel Parvoviruses in Frugivorous New and Old World Bats". Laboratory of Experimental Virology, Department of Medical Microbiology, Academic Medical Centre (AMC), Dec. 2011, pp. 1-3. [Accessed at http://www.ncbi.nlm.nih.gov/nuccore/jq037754 on May 16, 2014].
GenBank Accession No. JX896318, Xiao et al., "Identification of a new porcine parvovirus: an evidence for the coexistence of different intermediates during the evolution of parvovirus". College of Veterinary Medicine, Iowa State University, Department of Veterinary Diagnostic and Production Animal Medicine, Oct. 2012, pp. 1-4.
GenBank Accession No. JX896321.1, Xiao et al., "Porcine parvovirus 5 isolate IA469 clone 1, complete genome". College of Veterinary Medicine, Iowa State University, Department of Veterinary Diagnostic and Production Animal Medicine, 2013, pp. 1-3.
Gorodkin et al., "Porcine transcriptome analysis based on 97 non-normalized cDNA libraries and assembly of 1,021,891 expressed sequence tags". Genome Biology, vol. 8, No. 4, Apr. 2007, pp. R45.1-R45.16.
Huang et al., "Detection of a novel porcine parvovirus, PPV4, in chinese swine herds". Virology Journal, vol. 7, No. 1, 333, Nov. 2010, pp. 1-4.
International Search Report and Written Opinion for PCT/US2014/016165 dated Jun. 24, 2014.
Józwik et al., "Vaccination against porcine parvovirus protects against disease, but does not prevent infection and virus shedding after challenge infection with a heterologous virus strain". Journal of General Virology, vol. 90, No. 10, Jun. 2009, pp. 2437-2441.
Lytle et al., "Predicted Inactivation of Viruses of Relevance to Biodefense by Solar Radiation". Journal of Virology, vol. 79, No. 22, Nov. 2005, pp. 14244-14252.
Ma et al., "The immune enhancement of propolis adjuvant on inactivated porcine parvovirus vaccine in guinea pig". Cellular Immunology, vol. 270, 2011, pp. 13-18.
Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.
Wang et al., "Enhancing immune responses to inactivated porcine parvovirus oil emulsion vaccine by co-inoculating porcine transfer factor in mice". Vaccine, vol. 30, 2012, pp. 5246-52520.
Wu et al., "First complete genomic characterization of a porcine parvovirus 5 isolate from China". Archives of Virology, Dec. 2013, pp. 1-4.
Xiao et al., "Characterization of a Novel Porcine Parvovirus Tentatively Designated PPV5". PLOS One, vol. 8, No. 6, e65312, Jun. 2013, pp. 1-11.
Xiao et al., "Complete Genome Sequence of a Novel Porcine Parvovirus (PPV) Provisionally Designated PPV5". Genome Announcements, vol. 1, Issue 1, e00021-12, Jan./Feb. 2013, pp. 1-2.
Martinez et al., "Production of porcine parvovirus empty capsids with high immunogenic activity". Vaccine, vol. 10, No. 10, 1992, pp. 684-690.
GenBank Accession No. JX896320.1, Xiao et al., "Complete Genome Sequence of a Novel Porcine Parvovirus (PPV) Provisionally Designated PPV5". Genome Announcement, vol. 1, No. 1, E00021-12, 2012, pp. 1-3.

FIG. 1:
PPV5B DNA Sequence

PPV5B_Reference:

```
gene            935..2024
                /label="Predicted replicase"
gene            2161..2860
                /label="Predicted gene of unknown function / ORF3"
gene            2861..5014
                /label="Predicted Capsid"
Sequence:
    GCTTCAAGTCTATTAATTTGCATAATTTATGCAAAGAGGAAGTTAACCTGATTGGTCAGTTTTTT
    GGCGGGAAGCAATTTGATTGGACGGGAACTCAAGTCCTAATTTGCATTGACGTGGACCAATCAGA
    ATTGAGTACATATTATATAAGGAGGCCGAAAAAGAGGAAGTTTGTCATTTGCGTTTTGGAGACCA
    TCGCGAGCAGAACTCCGTCGTTTTCGGCCTGTATTTGAAGATGGAAACCTACTGGACAGGTATTT
    GCAGACTTTTTCCTGATGTTTTAAAAATACCTGGTGTTTATGAAGGACGCTATATTTTGAAGTT
    CCTGTTTCTACCAGAGACTTTATGAAATGGCCTGATATATTTCAAAATGAAAAAAATAATGAAAA
    CTGTGAGTCTGGCGCGGCGCCTGCGGCGCCGCGCGATGAAATTGACAGTAATCTAGTAACGGCTG
    TTAGACAAGGGGAGGCTCTATTTAGAGAGCTTCAAAAAGAACTTAGAAAATCCTGTAGATTAGGA
    GTAGATCCTGGCATTTTCATGCAATTGGAAAGAGTTGACTCAAAAGGTGGCTTACATTTGCATTG
    GTGTGTGTCTGTGTCCGCTGGTACCCCGCGAGATGTTTAACTATATTCAAAAATACAGAAAAAA
    AAGTTTCATTATATTACTTTGGTGTTGAGGGACTTAGCTTTTTTGTGCCACACAAAAATAAACAC
    GGAGCATGGAAAAGCACAGATGAAGGGTTTATTTATAATTATTTGCTAAAAAAACTACCACTGAA
    AGAATGTCTTTATGCATGGACTACAATTGGAGGTACAATAGGTGAAGCCTGTTAAATACAGAAA
    AAAGAAAAGAACTATTAGATAATAGACAAGATCCAGCAGTTATTGAAGAATTATCTGCTCCCATG
    TACAAATGTGCCACTGGAGAAAAAATGCTAGACATTGTACAGTGGTTGGTAGACAATAATATTTG
    TTCTGAATCCAGATGGGAGGGAAAAAATGCTCTAAGCTTATACTCATTCTTAGCCACACAAGCTG
    GAGGATATATCGCAAAACAATGCTTGAGAATCGCTCAGCAAAAATTACTAAAAGAAAAATCACTA
    GGGTTAACCTTAATGGATTTAAAAACATGGATGCTTTAAGAGCTTTCCAACAAAGTGACATGGA
    GTGCTCATTCGATCATAACAGAATACATTACATTTTTGCAGCTAACAACTATGATCCTAAAATTG
    CTGCAGTTATAATGTTTCACTGGAGCATGAAACAAACGGGAAAAAGAAACTGTGTATGGTTTTAC
    GGTCCTGCTACAACAGGAAAAACAAATATTGCACAGGCAATCTGCCATAGCTCAGCTAATTATGG
    CAATGTTAACTGGAACAATCCAAATTTTCCTTTTCAAGATATTGTAGGAGCTCAGGTAGGGTGGT
    GGGAAGAAGGGAAAATGACAGGAGACATGGTAGAAGCTGCAAAAGCTTTGCTGGGGGGAACTGCT
    TTGCGCATCGACCGCAAATGTATGCAATCTGTTGAAGTCAACAGTCCACCGTTTATTATAACATC
    GAATGTGGACATGACCGTGGTTCAAGAAGGAAGTTTTGTAAGCTTTGAACACCAACAGCCGTTAG
    AGGACAGGATGATAAAATTTTCATTTAACCTGACACTACCTGGAAACTTTGGTCTGATTACAACT
    GAAGAAGTGAAATCTTTTTCCGGATGGGTGCAAAACTTTCAGTTAAACCTGAAATCATGAATTG
    CCAAATTTTCAAAAGAGGACCTGCCAGCATCCGCCACCTAGTTCCTCTTGGAGAAATTCCTCCAC
    CAAAGGAGATGCATAAAAAACGACAGCCACTCTATTTGAGAGCTGAACCAGATGAAGAACAAGAA
    ACACCAGACGTCTTGGATCATTGGTTTGAAGAACCAAGTCAAAAAGAAAGAAGACAGAAGACCC
    TGCAAACACGACACCTCCTGCGGCTTATGAGAATTTAGATGACAACTTTGAACCTGTTCCAGGTA
    AGAATTTTGCATTTATCATTTTTTAATGTTCCAAAACAATAGAGCAAACTGGTGATATGTGCATA
    ATTCTTACAGATAGCCAAGTGAACCTGATATTTGACGTGGTCTACGAAGAGACACCAGAGGTGGA
    CGAAGTGGAGGAACAATGAGCTTTAGTGGGTATTCTAAAAATCTCCCCCCGGGTTTAGAGGAAGT
    TACATTCCCATTTTGGGTTGATTTTTGCTTGCCAGAATAGCTGATTTTATTAATTGGTGTGGGT
    ATTATAATATTAAATGTCCAGAAGCAGAAAAGGTATTTAGTATTGGACAATCTACACAGGTTTTA
    CTTAAATGGCCGGGTGCACAGGGAAAAGAAAACCGAGTTAAGAACTTTACCGAAGCTGCGTTTCC
```

FIG. 1 Cont.:

```
ATATATGAAAGTACCTGTGAGACCAGACAACATTGAATGGATTAAAATCCATGAGATGCTACATA
ATTATGATAGACAAATAACACCGCAGACAACTGAGAATGATTTACTTGCAGCTATCACTGCTGAC
TTCGATCAGAGAGAGATCATCCATCCAGTCACCGGCGAGAAATGGGTTTTCGGTAAGAAAACAGA
AGCTTTTGCTACTGATTTGGAAGAAGCCGTGGATGAAGAAGATCCTGATACAGAGAAAAACAAC
CTACTGATAAAACACAAAGTAATAACAAGAAAGGGGAAATTGGTGAAAAGAAAGAAGAAGGTGAT
ACCCTTACGTCAAATGAGGAACATCACCAATCAAGAAAACTATTAGAACACGACTCAAGCGAAGA
ACAACCAGAAGAAGCTGGTCACCGAGAACAGAAAGAACTAGAAGACAATATTGAAGACATCAAAC
ATGGAGCGGGAGAAGACCAAACCGGAACCGGTATCAACTGGCCAGGACATCGCTACACAGGTCCT
GGAAATCCACTCCCTCACGGAGCTCCTCGCAATGAAATTGATCTCTCTGCTGCGAAACATGATAT
CAGGTACAAACAATATTCTCGATATGGTCACTGGCCATACATTTGGGCGCCATATATTGATAAAA
AAATGCAAGAAGATATTAGAGAGATAGTAAAAAAAGGTTTAGGATTAGAAGGTAAACTTTTAGGT
AACCTTATATCAGCTTTATGGCAAGCAAAATACAGATTAGGAGCCCCGATATATGAAATTTTAAA
AACAATTTTACCCCCGAAAAGTATGCCTACTAAAGAATCTGTAGAAAAACATTTACCAAAACCTT
TGCCCATTGATCCTCCACAGACATCCTTACCAGGTGCATCTCCTCCTCGAACTCCTGACTTGGGT
GGCGAGACTGGAATGAATGAAGAGCCTCCAGCAAAAAGAAGAATGACAGAAGACAGATGTGACAG
CACCACAAGGTGCGAAACATTGGACACACAATATGAGGATTCTAAAATGGCGGGAGGGGGTGGGG
GGGGAGGGAATCAACCTAAAAGTTCTTGGATTGGGGGGGCTTTCTTTACTGATACGACGGTTACT
ACTTATGGTACTAGAAGGTGTGTGCTTAGCTCTTTTCCGCATAACTACTGCACCACAGAGAGCGG
GGATCATATACCTAGCCTTGTTGTCTGTACTCCATGGTACTATTATGATCTTAACATTCTATCAG
CTCATTTCTCTCCCTCTGCTTGGCAAACGCTTTTAGAAGAGTATGATGCTTTTAAACCTTTAAAA
TTGGAAGTTAAAATTAAAGAGATAGTTGTTAAAGATGTTAATAATATGACAGGGAAACAATGCTG
TGACACAGTTTCTGACAATGCCATGGCTGCAGTGCTGTGTTTTGAGGATACACATTACGAGCTGC
CATATGTTTTGGGAGGGGGACAGCTAACAGTGCCTGGTCATCTTCCAGGACAAACTTATGAACTT
CCAAAATACTGCTATAGAACTGTGGGAAAACCGCATAGCGAGATGTGGTCACCTGTAGATGGTTC
CAAAAGAGCCCACTTAGACATGCCTTTTGTTCAGCCAACACAGAACACTGAGTTCTTTATTTTAG
AGAACAGACACTCTACCATCCTTCACACAGGCAATGAATTCTTTCAAACCTATGACTTTCCAGAT
TTACATTTTGAGCAGCTAACACAGTACATGTGGGACGCGAGGAGACTTGACAATCCAATGAAAGG
TCAAAGAATACAGGTTATGAAAAACAAACCTACAGAAAACAAAGATCAAATGTTTGGTATCAGAG
CTTCGAGTTACCTCGTTCCCTGGATTGTCAACTCTCTAAACAGACCTGCTATGTTTTACAAGGA
GGAAGATTAAAAGACGGGGATTATTCCATTGTTGGGCCTGGGACCAGAGAACAGGCGACATACCA
CTACTTTAATGATACACCTGTCGTGGTTGAAAGAGATATTTACAAATTTACAACTAGTATGCTTA
AAAGAGAAACTCAACAGCCAGGACCGAGAACACAGGAAACAACGGTAAAAACACCTGATGGGACC
ATAATTATAACAACTAACAGTTTAGCGTATGGACAGGTGCCTGAAAACATTGATAACATACCGAG
TGATCACAAAGCCGCTTTCGGGGTTACAGGGTACAGGCTTGCTGTCGCTGAACAGAGAGGGTATA
GCACACCTGGAATGCCTTCTCATATAAGGGAGATATTATTGACAAAACACCGAAACTATTAGAA
AAAGATCAGCAAGAAATCACATTTCCAAACTTTGAAGGGTCTGTCAGCGAAAAACTTCCGCTAA
TCTAGAGTCTCAGATTTGGCTTATATCCCTAACACTGATAACAAACATAACTGCGGAACGCCCC
CTTTATCTATATGGGGAATGGAAAATCCTCCACCTATGGTTTTTTTGAGGTTACTCCCTCAACTG
GGACCCCCTGAAAAATCCAGCTGTTCTGGAAGCAAACCTTCTAAAAAGTTCTTGAATCAGTACTG
CCAATTTTTACTGGAATATACTGTAACATGGGCTGTTGTGAGGCGAAAGAAACATACTCCGAGGT
GGAACCCTATGCCGGGGGTCACAATTCCAACTTATAACAACGATCCTGTGTACATCCTTGACCAA
AATGGATTTTATAAATTGCCAGAAACTGTTTGGACAGCAAAGCAACGTGTTAGAGCGCGAAGATA
ATAAAAAAAAATTTGAGAAAAAAAAGTTACTTCCTCTTTTTTTTGAATTTGAAAAGCGCCAGG
CCTCTCGCCGGTCGCCCCTGACGTCACATCCGCTTCCGGGTCAAGGGCGGGGTCAAAGGTCAAA
GGTCTTCATACGTCATATCCGCTTCCGGGTCATGACC
```

Fig. 2:
PPV5B REPLICASE PROTEIN SEQUENCE

```
METYWTGICRLFPDVLKIPGVYEGRYIFEVPVSTRDFMKWPDIFQNEKNNENCESGAAPAAPRDEIDSNL
VTAVRQGEALFRELQKELRKSCRLGVDPGIFMQLERVDSKGGLHLHWCVSVSAGTPRDVLTIFKNTEKKV
SLYYFGVEGLSFFVPHKNKHGAWKSTDEGFIYNYLLKKLPLKECLYAWTTIGGTIGEACLNTEKRKELLD
NRQDPAVIEELSAPMYKCATGEKMLDIVQWLVDNNICSESRWEGKNALSLYSFLATQAGGYMAKQCLRIA
QQKLLKEKSLGLTLMDFKNMDALRAFQQSDMECSFDHNRIHYIFAANNYDPKIAAVIMFHWSMKQTGKRN
CVWFYGPATTGKTNIAQAICHSSANYGNVNWNNPNFPFQDIVGAQVGWWEEGKMTGDMVEAAKALLGGTA
LRIDRKCMQSVEVNSPPFIITSNVDMTVVQEGSFVSFEHQQPLEDRMIKFSFNLTLPGNFGLITTEEVKS
FFRMGAKLSVKPEIMNCQIFKRGPASIRHLVPLGEIPPPKEMHKKRQPLYLRAEPDEEQETPDVLDHWFE
EPSQKRKKTEDPANTTPPAAYENLDDNFEPVPGKNFAFIIF
```

Fig. 3:
PPV5B ORF3

MSFSGYSKNLPPGLEEVTFPFWVDFLLARIADFINWCGYYNIKCPEAEKVFSIGQSTQVLLKWPGAQGKE
NRVKNFTEAAFPYMKVPVRPDNIEWIKIHEMLHNYDRQITPQTTENDLLAAITADFDQREIIHPVTGEKW
VFGKKTEAFATDLEEAVDEEDPDTEKKQPTDKTQSNNKKGEIGEKKEEGDTLTSNEEHHQSRKLLEHDSS
EEQPEEAGHREQKELEDNIEDIK

Fig. 4:
PPV5B CAPSID PROTEIN SEQUENCE

MLHNYDRQITPQTTENDLLAAITADFDQREIIHPVTGEKWVFGKKTEAFATDLEEAVDEEDPDTEKKQPT
DKTQSNNKKGEIGEKKEEGDTLTSNEEHHQSRKLLEHDSSEEQPEEAGHREQKELEDNIEDIKHGAGEDQ
TGTGINWPGHRYTGPGNPLPHGAPRNEIDLSAAKHDIRYKQYSRYGHWPYIWAPYIDKKMQEDIREIVKK
GLGLEGKLLGNLISALWQAKYRLGAPIYEILKTILPPKSMPTKESVEKHLPKPLPIDPPQTSLPGASPPR
TPDLGGETGMNEEPPAKRRMTEDRCDSTTRCETLDTQYEDSKMAGGGGGGGNQPKSSWIGGAFFTDTTVT
TYGTRRCVLSSFPHNYCTTESGDHIPSLVVCTPWYYYDLNILSAHFSPSAWQTLLEEYDAFKPLKLEVKI
KEIVVKDVNNMTGKQCCDTVSDNAMAAVLCFEDTHYELPYVLGGGQLTVPGHLPGQTYELPKYCYRTVGK
PHSEMWSPVDGSKRAHLDMPFVQPTQNTEFFILENRHSTILHTGNEFFQTYDFPDLHFEQLTQYMWDARR
LDNPMKGQRIQVMKNKPTENKDQMFGIRASSYLVPWIVNSLNRPAMFLQGGRLKDGDYSIVGPGTREQAT
YHYFNDTPVVVERDIYKFTTSMLKRETQQPGPRTQETTVKTPDGTIIITTNSLAYGQVPENIDNIPSDHK
AAFGVTGYRLAVAEQRGYSTPGMPSHIREILLTKTPKLLEKDQQEITFPNFEGSVSEKTSANLESQIWAY
IPNTDNKHNCGTPPLSIWGMENPPPMVFLRLLPQLGPPEKSSCSGSKPSKKFLNQYCQFLLEYTVTWAVV
RRKKHTPRWNPMPGVTIPTYNNDPVYILDQNGFYKLPETVWTAKQRVRARR

Fig. 5:

Phylogenetic analysis of VP1/CAP region of PPV5B

FIG. 7:

BLASTp results of PPV5B_Capsid vs. Total GenBank sequences.
Closest Match: Porcine Parvovirus 4 PPV4 -- GenBank Accession ID: AFM73881
Sequence Identities: 53% (367/690)
Sequence Homologies: 68% (468/690)

```
PPV5B    50   RYGHWPYIWAPYIDKKMQEDIREIVKKGLGLEGKLLGNLISALWQAKYRLGAPIYEILKT   109
              ++GHWP++WAP++D++M ++I+++K    L  KLL N I ALW+AK ++GAPIYEI+K
PPV4_     3   KHGHWPHLWAPFVDRQMSQEIQQVLKGSTKLSQKLLANFIIALWRAKEKIGAPIYEIVKG    62

PPV5B   110   ILPPKSMPTKESV-EKHLPKPLPIDPPQTSLPGASPPRTPDLGGETGMNEEPPAKRRMTE   168
              + P   T ES+     P P P  PQ    ASPP++P+    E M+     K    E
PPV4_    63   VFPSVDKKTVESLLPHPDPIPAPPSSPQRGSKRASPPQSPNAHDEDTMSGHKRQKTMEVE   122

PPV5B   169   DRCDSTTRCETLDTQYEDSKMAGGGGGGGNQPKSSWIGGAFFIDTTVTTYGTRRCVLSSF   228
                 CD +  C T +    D ++ G GGG  N+ K +W+GG  FIDT++ T+GTRRCVLS+F
PPV4_   123   SECDKSLLCPTQNAG-ADFELCGTGGGATNE-KGTWVGGTQFTDTSIRTFGTRRCVLSAF   180

PPV5B   229   PHNYCTTESGDHIPSLVVCTPWYYYDLNILSAHFSPSAWQTLLEEYDAFKPLKLEVKIKE   288
              P  YC+  SGD IPS++  TPWYYYDLNI+S HFSPSA+QTL+E+YDAF+P  L V +KE
PPV4_   181   PDTYCSMMSGDAIPSIIFNTPWYYYDLNIMSCHFSPSAFQTLIEDYDAFRPRSLTVHLKE   240

PPV5B   289   IVVKDVNNMTGKQCCDTVSDNAMAAVLCFEDTHYELPYVLGGGQLTVPGHLPGQTYELPK   348
              +V+KDV      G Q  + VSDN  A +L FED +YELPYVLGGGQ++VPGHLPGQ Y+LPK
PPV4_   241   LVIKDVCQQQGLQA-EQVSDNNSATLLAFEDVNYELPYVLGGGQVSVPGHLPGQPYQLPK   299

PPV5B   349   YCYRTVGKPHSEMWSPVDGSKRAHLDMPFVQP--------------TQNTEFFILENRHST   395
              Y YRTVGKP  S   +   H D   P             TQ+TEF+ILEN +T
PPV4_   300   YSYRTVGKPDPN--SGFVPGRNTHPDQGPGHPKASKTIWYSQYLETQDTEFYILENHKAT   357

PPV5B   396   ILHTGNEFFQTYDFPDLHFEQLTQYMWDARRLDNPMKGQRIQVMKNKPTENKDQMFGIRA   455
              ILH+GN F Q Y+FPDL FEQLTQYMWDARR DNP+  QRIQVM     +  + F I+
PPV4_   358   ILHSGNTFSQNYNFPDLPFEQLTQYMWDARRQDNPLIDQRIQVMSRMYDDGPQKTFAIKV   417

PPV5B   456   SSYLVPWIVNSLNRPAMFLQGGRLKDGDYSIVGPGTREQATYHYFNDTPVVVERDIYKFT   515
              + Y+VP+  V S +RPAMFL GGR KDGDYSI GPG RE+ ++ Y+ND P ++ RD Y F+
PPV4_   418   NPYIVPFTVKSTSRPAMFLAGGRFKDGDYSITGPGDREKTSFRYYNDPPWIITRDTYLFS   477

PPV5B   516   TSMLKRETQQPGPRTQETTVKTPDGTIIITTNSLAYGQVPENIDNIPSDHKAAFGVTGYR   575
              + +  K E +QPGPR  +T V+TPDGT+I+TTN+LAYG   E +  NIP       GV   +R
PPV4_   478   SDLAKTEREQPGPRQGDTVVRTPDGTLIVTTNALAYGYTTEYLKNIPLLSSKYHGVENFR   537

PPV5B   576   LAVAEQRGYSTPGMPSHIREILLT--KTPKLL---------EKDQQEITFPNFEGSVSEKTSA   627
              LAV  +RGYS PG PSHIRE L    K P  +       E  ++EITFP++ GSV+EKT+A
PPV4_   538   LAVENERGYSMPGHPSHIRETLFRGKLPSEIRESTIKSEDQRKEITFPDYMGSVNEKTTA   597

PPV5B   628   NLESQIWAYIPNTDNKHNCGTPPLSIWGMENPPPMVFLRLLPQLGPPEKSSCSGSKPSKK   687
              NLESQIW+ IPNTD    C TPPLSIWGM+NPPPMVFLRLL Q+GPP +S+CSGS PS
PPV4_   598   NLESQIWSQIPNTDITEKCTTPPLSIWGMKNPPPMVFLRLLAQMGPPRRSACSGSIPSNT   657

PPV5B   688   FLNQYCQFLLEYTVTWAVVRRKKHTPRWNP    717
              +LNQYCQFLL Y + W V++R + T RWNP
PPV4_   658   YLNQYCQFLLTYEMEWDVIKRTRKTVRWNP    687
```

FIG. 8:

```
BLASTp results of PPV5B_REP gene vs. Total GenBank sequences.
Closest Match: Porcine Parvovirus 4 PPV4 -- GenBank Accession ID: ADF59557
Sequence Identities: 87% (517/597)
Sequence Homologies: 93% (555/597)

Query    1    METYWTGICRLFPDVLKIPGVYEGRYIFEVPVSTRDFMKWPDIFQNEKNNENCESGAAPA    60
              METYWTGICRLFPDVLKIPGVYEGRYIFEVP+STRD MKWPDIF NE N+EN +SGAAPA
Sbjct    1    METYWTGICRLFPDVLKIPGVYEGRYIFEVPISTRDCMKWPDIFGNENNSENQQSGAAPA    60

Query    61   APRDEIDSNLVTAVRQGEALFRELQKELRKSCRLGVDPGIFMQLERVDSKGGLHLHWCVS   120
              APR+ ++SNLV AVRQ EALFRELQKELRKSCRLGVDPGIFMQLE VDSKGGLHLHWCVS
Sbjct    61   APRENLNSNLVIAVRQAEALFRELQKELRKSCRLGVDPGIFMQLEEVDSKGGLHLHWCVS   120

Query    121  VSAGTPRDVLTIFKNTEKKVSLYYFGVEGLSFFVPHKNKHGAWKSTDEGFIYNYLLKKLP   180
              VSAGTPRDVLTIFKNTEKKVSLYYFGVEGLSFFVPHKNKHGAWKSTDEGFIYNYLLKKLP
Sbjct    121  VSAGTPRDVLTIFKNTEKKVSLYYFGVEGLSFFVPHKNKHGAWKSTDEGFIYNYLLKKLP   180

Query    181  LKECLYAWTTIGGTIGEACLNTEKRKELLDNRQDPAVIEELSAPMYKCATGEKMLDIVQW   240
              LKECLYAWTTIGG IG+ACLNT+KRKELLDNRQDPAVIEELSAPMYKCATGEKMLDIVQW
Sbjct    181  LKECLYAWTTIGGAIGDACLNTDKRKELLDNRQDPAVIEELSAPMYKCATGEKMLDIVQW   240

Query    241  LVDNNICSESRWEGKNALSLYSFLATQAGGYMAKQCLRIAQQKLLKEKSLGLTLMDFKNM   300
              LVDNNICSESRWE KNALSLYSFLATQAGGYMAKQCLRIAQQKLLKEK LGLTLM+FK+M
Sbjct    241  LVDNNICSESRWENKNALSLYSFLATQAGGYMAKQCLRIAQQKLLKEKPLGLTLMEFKDM   300

Query    301  DALRAFQQSDMECSFDHNRIHYIFAANNYDPKIAAVIMFHWSMKQTGKRNCVWFYGPATT   360
              +ALR FQQ + E +FD+NR+HYIFA NNYDPKIA+VIM+ WSMKQTGKRNCVWFYGPATT
Sbjct    301  NALRRFQQDEGEMTFDNNRMHYIFAINNYDPKIASVIMYFWSMKQTGKRNCVWFYGPATT   360

Query    361  GKTNIAQAICHSSANYGNVNWNNPNFPFQDIVGAQVGWWEEGKMTGDMVEAAKALLGGTA   420
              GKTN+AQAICHSSANYGNVNWNN NFPFQDIVGAQVGWWEEGKMTGDMVEAAKALLGGTA
Sbjct    361  GKTNMAQAICHSSANYGNVNWNNANFPFQDIVGAQVGWWEEGKMTGDMVEAAKALLGGTA   420

Query    421  LRIDRKCMQSVEVNSPPFIITSNVDMTVVQEGSFVSFEHQQPLEDRMIKFSFNLTLPGNF   480
              LRIDRKCMQS+EVNSPPF+ITSNVDMT+VQEGSFVSFEHQQPLEDRMIKFSFN+TLPGNF
Sbjct    421  LRIDRKCMQSIEVNSPPFLITSNVDMTIVQEGSFVSFEHQQPLEDRMIKFSFNMTLPGNF   480

Query    481  GLITTEEVKSFFRMGAKLSVKPEIMNCQIFKRGPASIRHLVPLGEIPPPKEMHKKRQPLY   540
              GLIT+EEVKSFFRMGAKL+ +P+IMNC IFK+GPASIRHLVP+GEIPPPKEM  KRQPLY
Sbjct    481  GLITSEEVKSFFRMGAKLAAQPDIMNCPIFKKGPASIRHLVPVGEIPPPKEMHKRQPLY   540

Query    541  LRAEPDEEQETPDVLDHWFEE--PSQKRKKTEDPANTTPPAAYENLDDN-FEPVPGK    594
              +RAEPDE Q+ P+ LDHWFEE   P +K++KT++ A    P   E + + F P PGK
Sbjct    541  MRAEPDEIQDNPEELDHWFEEEAPRKKKQKTKNTATKNPAETVEIIETEFIPAPGK    597
```

PORCINE PARVOVIRUS 5B, METHODS OF USE AND VACCINE

SEQUENCE LISTING

This application contains a sequence listing in accordance with 37 C.F.R. 1.821-1.825. The sequence listing accompanying this application is hereby incorporated by reference in its entirety. Said ASCII copy, created on Mar. 11, 2013, is named 10-0153-US-3-SEQ.txt and is 34,487 bytes in size.

BACKGROUND OF THE INVENTION

A. Field of the Invention

The present invention is in the field of animal health and relates to novel porcine *parvovirus* strains, including attenuated strains for vaccination, methods of manufacture and methods of treatment using vaccines obtained from said novel *parvovirus* strains.

B. Description of the Related Art

Parvoviruses infect a wide variety of animal species, and some of them are responsible for severe clinical diseases, but the majority of these viruses cause only mild or subclinical infections. They belong to the family Parvoviridae and form two subfamilies: Densovirinae, whose members infect insects, and Parvovirinae, whose members infect vertebrates. The latter subfamily currently includes five genera: *Dependovirus, Erythrovirus, Amdovirus, Bocavirus* and *Parvovirus* (1).

*Parvovirus* virions are non-enveloped and contain single-stranded, linear DNA genomes of approximately 5-6 kilobases (kb). The genome consists of two main open reading frames (ORF) that encode the non-structural and capsid proteins. The newly described bocaviruses carry a third ORF, between the two major ORFs (1).

The classical porcine parvovirus (PPV1) strains of the genus *Parvovirus* are widely distributed around the world and are responsible for reproductive disorders of pigs, especially in herds where vaccination protocols are not followed correctly or vaccine efficacy is decreased due to immunosuppressive factors. During the last decade, a number of new parvoviruses have been detected in pigs. These include porcine parvovirus 2 (PPV2) (2) and related viruses (3). A new group of porcine and bovine parvoviruses, namely the hokoviruses (PHoV, BHoV), were identified in Hong Kong (4), and these viruses were found to be genetically similar to human PARV4 and 5. Although they were originally named hokoviruses after Hong Kong, a new classification of PHoV as PPV3 was proposed (5). PPV4 shows the highest similarity to bovine parvovirus 2, but the coding capacity and genome organization are similar to those of bocaviruses, as PPV4 encodes an additional ORF3 like bocaviruses, located between ORF1 and ORF2. The PPV4-encoded putative ORF3 protein, however, is quite different from that of bocaviruses (5).

There is an ongoing need to monitor swine for the emergence of new viruses, and to develop vaccines, treatments and methods of detection for new viruses.

SUMMARY OF THE INVENTION

The present invention provides novel nucleotides sequences, protein sequences, immunogenic compositions, vaccines, and methods that relate to making and using new *parvovirus* strains that infect, inter alia, domestic swine. These strains are related to the novel porcine *parvovirus* identified in tissue samples from clinically diseased domestic swine; based on sequence homology with known porcine *parvovirus* species and strains, the novel virus was denominated porcine parvovirus 5B or PPV5B.

The compositions and methods of the invention provide for the detection of infections by said new virus, monitoring genetic changes in the viral sequences in wild and domestic animals and herds, and making and using novel vaccines for protecting animals from infection by the virus.

Immunogenic compositions and vaccines of the invention comprise polypeptide sequences encoded by the nucleic acid sequence of SEQ ID NO:1, or immunogenic fragments thereof, optionally including adjuvants for inducing a more robust immunogenic response.

Exemplary compositions of the invention comprise any one of the polypeptide sequences of SEQ ID NO:2, SEQ ID NO:3, SEQ NO:4, or fragments thereof that are immunoreactive to antibodies specific for PPV5B. Preferred polypeptides of the invention include the sequences of SEQ ID NO:4. Preferably those polypeptides, or fragments thereof, are immunoreactive to antibodies specific for PPV5B.

In another aspect the invention provides nucleic acid sequences that encode one or more polypeptides, antibody constructs, or antibody conjugates. The gene sequences coding for the polypeptides comprise a nucleic acid sequence that is at least 95%, 90%, 85%, or even 80% homologous to and/or identical with the sequence of SEQ ID NO: 1, in particular, nucleotide sequences 2861-5014 of SEQ ID NO:1 (the capsid protein), or fragments of SEQ ID NO:1 coding for a polypeptide that is immunoreactive to antibodies specific for PPV5B. Exemplary nucleic acid sequences of the invention include any one of the sequences of nucleotides 935-2024 of SEQ ID NO:1, nucleotides 2161-2860 of SEQ ID NO:1, and nucleotides 2861-5014 of SEQ ID NO:1, and fragments thereof, that encode a polypeptide that is immunoreactive to an antibody specific for PPV5B. Preferably, the nucleic acid sequences, or genes, are those coding for a polypeptide or peptide that is immunoreactive to an antibody specific for PPV5B.

Moreover a polypeptide of the invention as used herein includes but is not limited to a polypeptide that comprises:
  i) a polypeptide comprising the amino acid sequence of SEQ ID NO:2, SEQ ID NO:3 or SEQ ID NO:4;
  ii) a polypeptide that is at least 80% homologous to and/or identical with a polypeptide of i);
  iii) a fragment of the polypeptides of i) and/or ii);
  iv) a fragment of iii) or iv) comprising at least 13, preferably 15, more preferably 17, even more preferably 20 contiguous amino acids included in the sequences of SEQ ID NO:3 or SEQ ID NO:4;
  v) a polypeptide that is encoded by a polynucleotide comprising the sequence of nucleotides 935-2024 of SEQ ID NO:1 nucleotides 2161-2860 of SEQ ID NO:1, or nucleotides 2861-5014 of SEQ ID NO:1;
  vi) a polypeptide that is encoded by a polynucleotide that is at least 80% homologous to or identical with polynucleotide of vi);
  vii) a protein fragment that is encoded by a polynucleotide that comprises at least 39, preferably 45, more preferably 51, even more preferably 60 contiguous nucleotides included in the sequences of nucleotides 2161-2860 of SEQ ID NO:1, or nucleotides 2861-5014 of SEQ ID NO:1.

Immunogenic compositions of the invention which comprise at least one or more PPV5B polypeptides as defined herein may further comprise a physiologically-acceptable vehicle such as a pharmaceutically or veterinary-acceptable carrier, adjuvant, or combination thereof.

Any of the PPV5B polypeptides provided herewith or any immunogenic compositions comprising one or more of these PPV5B polypeptides provided herewith can be used as a medicament, preferably as a vaccine or immunogenic composition, most preferably for the prophylaxis or treatment of a subject against a PPV5B infection.

Particularly preferred PPV5B polypeptides include those with immunogenic epitopes that induce an immunological response that is specific for PPV5B. Preferred PPVB polypeptides include those having an amino acid sequences predicted in related PPV1 to be surface antigens (Simpson et al. JMB 315, 2002) and include, but is not limited to residues 289, 375-381 and 431-443 of SEQ ID NO:4.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include veterinary-acceptable carriers, diluents, isotonic agents, stabilizers, or adjuvants.

Methods of the invention include, but are not limited to, a method of provoking an immune response against a PPV5B infection in a subject comprising the step of administering to the subject an immunogenic composition comprising one or more PPV5B polypeptides as defined herein. Preferably, the immune response is provoked against more than one serotype or strain of PPV5B. Compositions of the invention may be used to treat or alternatively to prevent a PPV5B infection. Preferably, such immune response reduces the incidence of or severity of one or more clinical signs associated with or caused by the infection with one or more PPV5B serotypes.

Herein, suitable subjects and subjects in need to which compositions of the invention may be administered include animals in need of either prophylactic or treatment for a viral, microbial, parasitic, protozoan, bacterial, or fungal associated infection, disease, or condition. Animals in which the immune response is stimulated by use of compositions or methods of the invention include livestock, such as porcine, bovine, poultry (e.g. chickens, ducks, geese, or turkeys) caprine, and ovine, and domestic animals, such as mice, rabbits, dogs, cats, and horses. Preferred animals include swine, murids, equids, lagomorphs, and bovids. Most preferably, an immune response is stimulated in swine.

The invention also provides a method of reducing the incidence of or severity of one or more clinical signs associated with or caused by PPV5B infection, comprising the step of administering an immunogenic composition of the invention that comprises one or more PPV5B peptides as provided herewith and preferably a carrier molecule, such that the incidence of or the severity of a clinical sign of the PPV5B infection is reduced by at least 10%, preferably at least 20%, even more preferred at least 30%, even more preferred at least 50%, even more preferred at least 70%, most preferred at least 100% relative to a subject that has not received the immunogenic composition as provided herewith. Such clinical signs include viremia and immunosuppression as a result from an infection with PPV5B alone. Such clinical signs may include neurological signs (depression, ataxia, lethargy), diarrhea, dyspnea, loss of body condition, swelling of joints (resulting in lameness and recumbency), decreased average daily weight gain, mortality, and polyserositis as a result of a co-infection with another organism, e.g., *Mycoplasma hyorhinis*.

According to a further aspect, the present invention also relates to a method for the prophylaxis of a PPV5B infection, wherein said PPV5B infection may be caused by PPV5B having 100% sequence identity with the nucleotide sequence of SEQ ID NO:1; having at least 95% sequence identity with the nucleotide sequence of SEQ ID NO:1; having at least 90% sequence identity with the nucleotide sequence of SEQ ID NO:1; or having at least 85% sequence identity with the nucleotide sequence of SEQ ID NO:1; comprising the step of administering an immunogenic composition of the invention that comprises one or more PPV5B peptides as provided herewith, i.e., at least one polypeptide having 100%, at least 95%, at least 90% and/or at least 85% sequence identity with, respectively, polypeptide sequences of SEQ ID NO:3 and/or SEQ ID NO:4, or fragments there of comprising at least 12, preferably 15, more preferably 17, even more preferably 20 contiguous amino acids included in the sequences of SEQ ID NO:3 and/or SEQ ID NO:4.

The invention also provides a method of preparing any of the immunogenic compositions provided herewith that method comprises mixing one or more PPV5B peptides as provided herewith with a carrier molecule, preferably such that the one or more PPV5B peptides and carrier molecule are covalently coupled or conjugated to one another. Such conjugates may be multivalent or univalent. Multivalent compositions or vaccines include an immuno-conjugation of multiple PPV5B peptides with a carrier molecule. In a further aspect, the invention provides a method of producing one or more PPV5B peptides that method comprises transforming a host cell, preferably a prokaryotic cell such as *E. coli* with a nucleic acid molecule that codes for any of the PPV5B peptides as provided herewith. Alternatively, the host cell may be a eukaryotic cell such as an animal cell, an insect cell, a protist cell, a plant cell, or a fungal cell. Preferably the eukaryotic cell is a mammalian cell such as CHO, BHK or COS, or a fungal cell such as *Saccharomyces cerevisiae*, or an insect cell such as Sf9. Baculovirus expression of the nucleic acids of the instant invention are also preferred.

Another aspect of the invention provides a method of producing one or more PPV5B peptides that induce an immune response against at least one genetic variants of PPV5B and more preferably two or more genetic variants of PPV5B. This comprises culturing a transformed expression vector coding for and expressing one or more PPV5B peptides disclosed herein. The expressed proteins are either retained by the expression organism or secreted into the culture medium. Expression is conducted under conditions sufficient to produce a PPV5B peptide capable of inducing an immune response to PPV5B. The PPV5B serotypes to which the PPV5B peptides induce an immune response include but are not limited to sequences having at least 99, 98, 97, 96, 95, 94, 93, 92, 91 or 90% identity.

Methods of making compositions of the invention may further comprise admixing the conjugate of one or more PPV5B peptides and a carrier molecule with a physiologically-acceptable vehicle such as a pharmaceutically- or veterinary-acceptable carrier, adjuvant, or combination thereof. Those of skill in the art will recognize that the choice of vehicle, adjuvant, or combination will be determined by the delivery route, personal preference, and animal species among others.

In another aspect, the invention provides a method of diagnosing a PPV5B infection in a subject. That method comprises providing one or more PPV5B peptides; contacting the one or more PPV5B peptides with a sample obtained from the subject; and identifying the subject as having a PPV5B infection if an antibody capable of binding the one or more PPV5B peptides is detected in the sample.

In another respect, the invention provides a method of ascertaining that a subject has been previously exposed to a PPV5B infection and is able to express an immune response to PPV5B. That method comprises providing one or more PPV5B peptides; contacting the one or more PPV5B peptides with a sample obtained from the subject; and identifying the subject as having a PPV5B infection if an antibody capable of binding the one or more PPV5B peptides is detected in the sample.

The invention also provides kits that comprise an immunogenic composition that comprises one or more PPV5B peptides, preferably together with a carrier molecule; a container for packaging the immunogenic composition; a set of printed instructions; and a dispenser capable of administering the immunogenic composition to an animal. Optionally, the one or more PPV5B peptides and the carrier molecule may be packaged as a conjugate or as separate compounds. When supplied separately, a means of conjugating the one or more PPV5B peptides and carrier molecule, as well as appropriate printed instructions, is also supplied.

The invention also provides kits for vaccinating an animal comprising a set of printed instructions; a dispenser capable of administering the immunogenic composition provided herewith comprising one or more PPV5B peptides to an animal; and wherein at least one of PPV5B peptides effectively immunizes the animal against at least one disease associated with PPV5B infection. Preferably, the one or more PPV5B peptides are selected from those provided herewith. Kits of the invention may further comprise a veterinary acceptable carrier, adjuvant, or combination thereof.

The dispenser in a kit of the invention is capable of dispensing its contents as droplets; and the immunogenic composition comprises the PPV5B peptides as provided herewith included in the kit is capable of reducing the severity of at least one clinical sign of a PPV5B infection when administered intranasally, orally, intradermally, or intramuscularly to an animal. Preferably, the severity of a clinical sign is reduced by at least 10% preferably by at least 20%, even more preferred by at least 30%, even more preferred by at least 50%, even more preferred by at least 70%, most preferred by at least 100% as compared to an untreated, infected animal.

Methods for the treatment or prophylaxis of infections caused by PPV5B are also disclosed. The method comprises administering an effective amount of the immunogenic composition of the present invention to a subject, wherein said treatment or prophylaxis is selected from the group consisting of reducing signs of PPV5B infection, reducing the severity of or incidence of clinical signs of PPV5B infection, reducing the mortality of subjects from PPV5B infection, and combinations thereof.

Compositions of the invention further comprise a veterinary-acceptable carrier, adjuvant, or combination thereof. Such compositions may be used as a vaccine and comprise one or more additional attenuated vaccines, inactivated vaccines, or combinations thereof. Such vaccines elicit a protective immunological response against at least one disease associated with viruses selected from the group consisting of porcine parvoviruses 1, 2, 3, 4, 5A, 5B, other porcine *parvovirus* species, other porcine pathogenic viruses and bacteria, and combinations thereof. Other types of vaccines that could be co-administered in combination with a vaccine to PPV5B include, but are not limited to, porcine circovirus type 2 (e.g., INGELVAC® CircoFLEX, INGELVAC® CircoFLEX-MycoFLEX), porcine reproductive and respiratory syndrome virus (e.g., INGELVAC® PRRS ATP, INGELVAC® PRRSV MLV,), porcine parvovirus (e.g., REPROCYC® PRRSV-PLE), *Mycoplasma* (e.g., INGELVAC® MycoFLEX), etc.

Those of skill in the art will understand that the compositions used herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the immunogenic and vaccine compositions of the present invention can include pharmaceutical- or veterinary-acceptable carriers, diluents, isotonic agents, stabilizers, or adjuvants.

Methods of the invention may also comprise admixing a composition of the invention with a veterinarily acceptable carrier, adjuvant, or combination thereof. Those of skill in the art will recognize that the choice of carrier, adjuvant, or combination will be determined by the delivery route, personal preference, and animal species among others.

The invention also provides a method of reducing the severity of an ongoing PPV5B infection in an animal by administration of a composition to the animal. The composition may include an attenuated viral culture or one or more PPV5B peptides in combination with an acceptable veterinary carrier.

Preferred routes of administration include intranasal, oral (e.g., in drinking water), intradermal, and intramuscular. Intramuscular administration, most preferably in a single dose, is preferred. The skilled artisan will recognize that compositions of the invention may also be administered in two or more doses, as well as, by other routes of administration. For example, such other routes include subcutaneously, intracutaneously, intravenously, intravascularly, intraarterially, intraperitnoeally, intrathecally, intratracheally, intracutaneously, intracardially, intralobally, intramedullarly, intrapulmonarily, or intravaginally. Depending on the desired duration and effectiveness of the treatment, the compositions according to the invention may be administered once or several times, also intermittently, for instance on a daily basis for several days, weeks or months and in different dosages.

The invention also provides kits for vaccinating an animal comprising a set of printed instructions; a dispenser capable of administering a vaccine to an animal; and at least one isolate from a cell culture, including but not limited to a bacterial, fungal, insect or mammalian cell culture that effectively immunizes the animal against at least one disease associated with PPV5B, other *parvovirus* strains, other pathogens, and/or a combination thereof. Kits of the invention may further comprise a veterinary-acceptable carrier, adjuvant, or combination thereof.

The dispenser in a kit of the invention is capable of dispensing its contents as droplets; and the isolate included in the kit is capable of reducing the severity of at least one clinical sign of a PPV5B infection when administered intranasally, orally, intradermally, or intramuscularly to an animal. In some kits, the isolate is also capable of reducing the severity of at least one clinical sign of a PPV5B infection. Preferably, the severity of a clinical sign is reduced by at least 10% as compared to an untreated, infected animal.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The application contains at least one drawing executed in color. Copies of this patent application publication with color drawing(s) will be provided by the Office upon request and payment of the necessary fee.

FIG. 1. shows the nucleic acid sequence of PPV5B (SEQ ID NO:1).

FIG. 2. shows the protein sequence of the PPV5B replicase (SEQ ID NO:2).

FIG. 3. shows the protein sequence of the PPV5B open reading frame (ORF) protein (SEQ ID NO:3).

FIG. 4. shows the protein sequence of the PPV5B capsid protein (SEQ ID NO:4).

FIG. 5. shows pair-wise amino acid identity comparisons of the protein sequences of the PPV5B capsid protein and numerous other viral sequences. References for the viral sequences are listed in Table 1:

FIG. 7 shows identities of the PPV5B capsid protein (residues 184-851 of SEQ ID NO:4) to the closest related protein of PPV4 (GenBank accession # AFM73881 (SEQ ID NO: 5)), showing a sequence identity of 53% (367/690).

FIG. 8 shows identities of the PPV5B replicase protein (residues 1-594 of SEQ ID NO:2) to the closest related protein of PPV4 (GenBank accession #ADF59557 (SEQ ID NO: 11)), showing a sequence identity of 87% (517/597).

DETAILED DESCRIPTION

Figure 6:
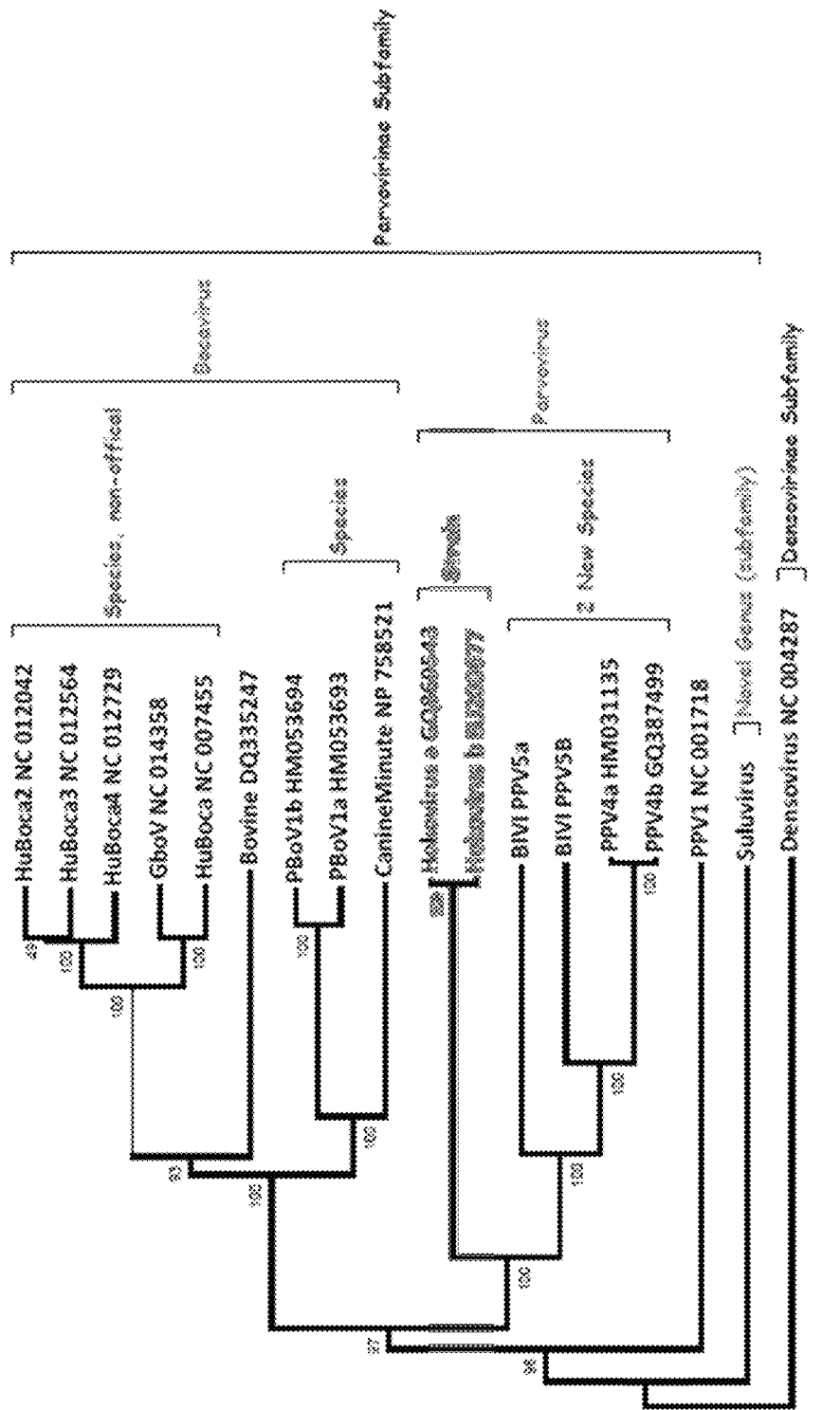
FIG. 6 shows a phylogenetic analysis of VP1/CAP region of PPV5B as compared with other viral VP1 and capsid proteins listed in Table 1.

The invention provides nucleic acids and fragments thereof, polypeptides and immunologically-effective fragments thereof, vaccines, immunologically-effective preparations, antibodies, diagnostic assays and kits, and methods of making and using said compositions and preparations, related to the herein-disclosed novel porcine parvovirus 5B and variants thereof.

The practice of the present invention will employ, unless otherwise indicated, conventional techniques of molecular biology, microbiology, recombinant DNA technology, protein chemistry and immunology, which are within the skill

TABLE 1

| Sequence | GenBank ID | Journal Info | Authors |
| --- | --- | --- | --- |
| [1] Bovine | DQ_335247 | J. Virol. 81 (21), 12080-12085 (2007) | Qiu, J., Cheng, F., Johnson, F. B. and Pintel, D |
| [2] CanineMinute | NP_758521 | Virology 302 (2), 219-223 (2002 | Schwartz, D., Green, B., Carmichael, L. E. and Parrish, C. R. |
| [3] GboV | NC_014358 | PLoS ONE 5 (7), E11948 (2010) | Kapoor, A., Mehta, N., Esper, F., Poljsak-Prijatelj, M., Quan, P. L., Qaisar, N., Delwart, E. and Lipkin, W. I |
| [4] PBoV1a | HM_053693 | PLoS ONE 5 (10), E13583 (2010) | Cheng, W. X., Li, J. S., Huang, C. P., Yao, D. P., Liu, N., Cui, S. X., Jin, Y. and Duan, Z. J. |
| [5] PBoV1b | HM_053694 | PLoS ONE 5 (10), E13583 (2010) | Cheng, W. X., Li, J. S., Huang, C. P., Yao, D. P., Liu, N., Cui, S. X., Jin, Y. and Duan, Z. J. |
| [6] HuBoca | NC_007455 | Proc. Natl. Acad. Sci. U.S.A. 102 (36), 12891-12896 (2005) | Allander, T., Tammi, M. T., Eriksson, M., Bjerkner, A., Tiveljung-Lindell, A. and Andersson, B. |
| [7] HuBoca2 | NC_012042 | J. Infect. Dis. 199 (2), 196-200 (2009 | Kapoor, A., Slikas, E., Simmonds, P., Chieochansin, T., Naeem, A., Shaukat, S., Alam, M. M., Sharif, S., Angez, M., Zaidi, S. and Delwart, E. |
| [8] HuBoca3 | NC_012564 | PLoS Pathog. 5 (4), E1000391 (2009) | Arthur, J. L., Higgins, G. D., Davidson, G. P., Givney, R. C. and Ratcliff, R. M. |
| [9] HuBoca4 | NC_012729 | J. Infect. Dis. 201 (11), 1633-1643 (2010) | Kapoor, A., Simmonds, P., Slikas, E., Li, L., Bodhidatta, L., Sethabutr, O., Triki, H., Bahri, O., Oderinde, B. S., Baba, M. M., Bukbuk, D. N., Besser, J., Bartkus, J. and Delwart, E. |
| [10] Densovirus | NC_004287 | DIRECT SUBMISSION TO GENBANK | Nonaka, K., Chiba, T., Nakahara, S., Kajiura, Z. and Nakagaki, M. |
| [11] Hokovirus_a | GQ_869543 | Virol. J. 7, 171 (2010) | Adlhoch, C., Kaiser, M., Ellerbrok, H. and Pauli, G. |
| [12] Hokovirus_b | EU_200677 | J. Gen. Virol. 89 (PT 8), 1840-1848 (2008) | Lau, S. K., Woo, P. C., Tse, H., Fu, C. T., Au, W. K., Chen, X. C., Tsoi, H. W., Tsang, T. H., Chan, J. S., Tsang, D. N., Li, K. S., Tse, C. W., Ng, T. K., Tsang, O. T., Zheng, B. J., Tam, S., Chan, K. H., Zhou, B. and Yuen, K. Y. |
| [13] PPV4a | HM_031135 | Virol. J. 7 (1), 333 (2010) | Huang, L., Zhai, S. L., Cheung, A. K., Zhang, H. B., Long, J. X. and Yuan, S. S |
| [14] PPV4b | GQ_387499 | Arch. Virol. 155 (5), 801-806 (2010) | Cheung, A. K., Wu, G., Wang, D., Bayles, D. O., Lager, K. M. and Vincent, A. L. |
| [15] PPV5B | | | |
| [16] PPV1 | NC_001718 | Virology 197 (1), 86-98 (1993) | Bergeron, J., Menezes, J. and Tijssen, P. | of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

A. Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

"Protection against disease," "protective immunity," "functional immunity" and similar phrases, means a response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection is lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of infection with PPV5B. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a significant reduction of one or more clinical symptoms which are associated with infection by an infectious agent, preferably PPV5B, in a vaccinated group of subjects vs. a non-vaccinated control group of subjects. The term "significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

An "immunogenic or immunological composition" refers to a composition of matter that comprises at least one PPV5B protein or polypeptide, or immunogenic portion thereof, that elicits an immunological response in the host of a cellular or antibody-mediated immune response to the composition. In a preferred embodiment of the present invention, an immunogenic composition induces an immune response and, more preferably, confers protective immunity against one or more of the clinical signs of a PPV5B infection.

An "immunogenic" PPV5B polypeptide, or "antigen" as used herein refer to a polypeptide or protein that elicits an immunological response as described herein. An "immunogenic" PPV5B protein or polypeptide includes the full-length sequence of any of the coding sequences identified herein or analogs or immunogenic fragments thereof. The term "immunogenic fragment" or "immunogenic portion" refers to a fragment or truncated and/or substituted form of an amino acid sequence of a PPV5B protein that includes one or more epitopes and thus elicits the immunological response described herein. In general, such truncated and/or substituted forms, or fragments will comprise or encode at least 13 contiguous amino acids from the full-length protein, e.g., the capsid protein. More preferably, the truncated or substituted forms, or fragments will have at least 15, more preferably at least 17, and still more preferably at least 20, and even more preferably 30 contiguous amino acids from the full-length protein, e.g., the capsid protein.

The term "epitope" means a segment or fragment of a composition of matter, e.g., a protein or polypeptide, which is recognized by the immune system, specifically by antibodies, B cells, or T cells. In the present invention, the epitope is generally a fragment or fragments of a polypeptide sequence of a viral protein.

Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, poly-epitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

Herein, "specifically immunoreactive" refers to an immunoreactive protein or polypeptide that recognizes an antigen characteristic of PPV5B infection but does not react with an antigen characteristic of a strict challenge control. To determine the specificity of a potential PPV5B immunoreactive protein or other polypeptide, various immunoassays (ELISA, IFA, WesternBlot) would be used to test the protein against animal sera containing genetically similar viruses. The protein would also be tested in various immunoassays against material containing proteins related to the expression method (Baculovirus, Sf9 cells, etc.).

As used herein, “a pharmaceutical- or veterinary-acceptable carrier” or “excipient” includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. “Adjuvants” as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of “Vaccine Design, The Subunit and Adjuvant Approach” edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 500 μg to about 5 mg per dose, more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Safety" refers to the absence of adverse consequences in a vaccinated animal following vaccination, including but not limited to: potential reversion of a live viral-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—an immune response in the animal against PPV5B.

"Mortality", in the context of the present invention, refers to death caused by PPV5B infection, and/or co-infections with other organisms which are potentiated by PPV5B infections, and includes the situation where the infection is so severe that an animal is euthanized to prevent suffering and provide a humane ending to its life.

"Attenuation" means reducing the virulence of a pathogen. In the present invention "attenuation" is synonymous with "avirulent." In the present invention, an attenuated virus is one in which the virulence has been reduced so that it does not cause clinical signs of a PPV5B infection but is capable of inducing an immune response in the target mammal, but may also mean that the clinical signs are reduced in incidence or severity in animals infected with the attenuated PPV5B in comparison with a "control group" of animals infected with non-attenuated PPV5B and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent PPV5B strain is one that suitable for incorporation into an immunogenic composition comprising a modified live PPV5B virus.

"Killed" or "inactivated" means treated with a physical or chemical agent which renders the PPV5B virus dead and/or otherwise incapable of reproduction. PPV5B may be killed by conventional means, such as, for example, heat, radiation or psoralen in the presence of ultraviolet light. PPV5B can be inactivated by conventional means such as, for example, through chemical inactivation using one or more chemical inactivating agents including, but not limited to, one or more of binary ethyleneimine (BEI), beta-propiolactone, formalin, gluteraldehyde, and/or sodium dodecyl sulfate. Methods of attenuating virulent strains of these viruses and methods of making an inactivated viral preparation are known in the art and are described in, e.g., U.S. Pat. Nos. 4,567,042 and 4,567,043. Antigens from PPV5B for use in the vaccine compositions of the present invention can thus be in the form of a whole virus which is a modified and/or attenuated live viral preparation or a killed or inactivated viral preparation, inter alia.

"Antibodies" as used herein includes anti-PPV5B antibodies, e.g., monoclonal and polyclonal antibodies, single chain antibodies, chimeric antibodies, humanized, human, porcine, and CDR-grafted antibodies, including compounds which include CDR sequences which specifically recognize a PPV5B polypeptide of the invention. The term "specific for" indicates that the variable regions of the antibodies of the invention recognize and bind a PPV5B polypeptide exclusively (i.e., are able to distinguish a single PPV5B polypeptide from related polypeptides despite sequence identity, homology, or similarity found in the family of polypeptides), and which are permitted (optionally) to interact with other proteins (for example, S. aureus protein A or other antibodies in ELISA techniques) through interactions with sequences outside the variable region of the antibodies, and in particular, in the constant region of the antibody molecule. Screening assays to determine binding specificity of an antibody of the invention are well known and routinely practiced in the art. For a comprehensive discussion of such assays, see Harlow et al. (Eds), Antibodies A Laboratory Manual: Cold Spring Harbor Laboratory; Cold Spring Harbor, N.Y. (1988), Chapter 6. Antibodies that recognize and bind fragments of the PPV5B polypeptides of the invention are also contemplated, provided that the antibodies are first and foremost specific for, as defined above, a PPV5B polypeptide of the invention from which the fragment was derived. For the purposes of clarity, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. Antibodies can exist in a variety of forms including, for example, as, Fv, Fab', F(ab')2, as well as in single chains, and include synthetic polypeptides that contain all or part of one or more antibody single chain polypeptide sequences.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount an attenuated live virus preparation, as measured by the number of plaque forming units (PFU) per dose or equivalent measure, is monitored by the median tissue culture infective dose (TCID50), i.e. the amount of a pathogenic agent that will produce pathological change in 50% of inoculated and susceptible cell cultures. For a killed vaccine or antigenic subunit, the effective amount refers to the relative antigen content (RAC), i.e. the inclusion level of antigen per effective dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

"Sequence identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences, with gaps introduced if necessary. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988); the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and BLASTX (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology" as used herein refers to a method of determining the relatedness of two sequences. To determine sequence homology, two or more sequences are optimally aligned, and gaps are introduced if necessary. However, in contrast to "sequence identity," conservative amino acid substitutions are also counted as a match when determining sequence homology. In other words, to obtain a polypeptide having 95% sequence homology with a reference sequence, 85%, preferably 90%, even more preferably 95% of the amino acid residues in the reference sequence must match or comprise a conservative substitution with another amino acid, or a number of amino acids up to 15%, preferably up to 10%, even more preferably up to 5% of the total amino acid residues, not including conservative substitutions, in the reference sequence may be inserted into the reference sequence. Preferably the homologous sequence comprises at least a stretch of 50, even more preferred of 100, even more preferred of 250, even more preferred of 500 nucleotides encoding homologous amino acids.

A "conservative substitution" refers to the substitution of an amino acid residue with another amino acid residue having similar characteristics or properties including size, hydrophobicity, etc., such that the overall functionality does not change significantly. It can also mean a nucleotide substitution that results in a conservative amino acid substitution.

B. Carrier Molecules

The carrier molecules to which the PPV5B proteins or peptides of the invention can be conjugated or covalently linked are preferably those described above. Preferred carriers for animal use are bovine serum albumin and Keyhole Limpet Hemocyanin. Preferably, the carrier protein itself is an immunogen.

The PPV5B proteins or peptides of the invention may be covalently coupled to the carrier by any convenient method known to the art. While use of a symmetric linker such as adipic acid dihydrazide, as described by Schneerson et al, J. Experimental Medicine, 152, 361-376 (1980), or a heterobifunctional linker such as N-succinimidyl 3-(2-pyridyldithio) propionate as described by Fattom et al, Infection and Immunity, 56, 2292-2298 (1988) are within the scope of the invention, it is preferred to avoid the use of any linker but instead couple a PPV5B peptide of the invention directly to the carrier molecule. Such coupling may be achieved by means of reductive amination as described by Landi et al J. Immunology, 127, 1011-1019 (1981).

The size of the immunogenic composition, as defined by average molecular weight, is variable and dependent upon the chosen PPV5B protein(s) or peptide(s) and the method of coupling of the PPV5B protein(s) or peptide(s) to the carrier. Therefore, it can be as small as 1,000 daltons ($10^3$) or greater than $10^6$ daltons. With the reductive amination coupling method, the molecular weight of the PPV5B protein(s) or peptide(s) is usually within the range of 5,000 to 500,000 or more; e.g., for the capsid protein of SEQ ID NO:4, the molecular weight is predicted to be approximately 101,000 daltons, which is predicted to form virus like particles (VLP) comprised of 60 monomeric proteins.

Carrier molecules, i.e. peptides, derivatives and analogs thereof, and peptide mimetics that specifically bind a PPV5B protein or peptide of the invention can be produced by various methods known in the art, including, but not limited to solid-phase synthesis or by solution (Nakanishi et al., 1993, Gene 137:51-56; Merrifield, 1963, J. Am. Chem. Soc. 15:2149-2154; Neurath, H. et al., Eds., The Proteins, Vol II, 3d Ed., p. 105-237, Academic Press, New York, N.Y. (1976), incorporated herein in their entirety by reference).

The PPV5B proteins or peptides of the invention or the antibodies or binding portions thereof of the present invention may be administered in injectable dosages by solution or suspension of in a diluent with a pharmaceutical or veterinary carrier.

Safety and efficacy of such molecules are determined by standard procedures in cell cultures or experimental animals as described and regulated by the Center for Veterinary Biologics (CVB). Toxicity and therapeutic efficacy of such molecules can be determined by standard pharmaceutical procedures in cell cultures or experimental animals, e.g., for determining the $LD_{50}$ (the dose lethal to 50% of the population).

The vaccines of the invention may be multivalent or univalent. Multivalent vaccines are made from immunoconjugation of multiple PPV5B proteins or peptides with a carrier molecule.

In one aspect, the PPV5B protein or peptide compositions comprise an effective immunizing amount of the immunogenic conjugate, preferably in combination with an immunostimulant; and a physiologically acceptable vehicle. As used in the present context, "immunostimulant" is intended to encompass any compound or composition which has the ability to enhance the activity of the immune system, whether it is a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of stimulant for a given vaccine. More than one immunostimulant may be used in a given formulation. The immunogen may also be incorporated into liposomes, or conjugated to polysaccharides and/or other polymers for use in a vaccine formulation.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig.

C. Adjuvants

In order to further increase the immunogenicity of the immunogenic compositions provided herewith, and which contain one or more PPV5B proteins or peptides may also comprise one or more adjuvants.

The adjuvant may be purified by any of the techniques described previously or known in the art. The preferred purification technique is silica gel chromatography, in particular the "flash" (rapid) chromatographic technique, as described by W. Clark Still et al, J. Organic Chemistry, 43, 2923-2925 (1978). However, other chromatographic methods, including HPLC, may be used for purification of the adjuvant. Crystallization may also be used to purify the adjuvant. In some cases, no purification is required as a product of analytical purity is obtained directly from the synthesis.

The vaccine compositions of the invention are prepared by physically mixing the adjuvant with the PPV5B protein(s) or peptide(s) under appropriate sterile conditions in accordance with known techniques to produce the adjuvanted composition. Complexation of the PPV5B proteins(s) or peptide(s) and the adjuvant is facilitated by the existence of a net negative charge on the conjugate which is electrostatically attracted to the positive charge present on the long chain alkyl compound adjuvant.

D. Physiologically-Acceptable Vehicles

The vaccine compositions of this invention may be formulated using techniques similar to those used for other pharmaceutical polypeptide compositions. Thus, the adjuvant and PPV5B protein(s) or peptide(s), preferably conjugated to carrier molecule and/or admixed with an adjuvant may be stored in lyophilized form and reconstituted in a physiologically acceptable vehicle to form a suspension prior to administration. Alternatively, the adjuvant and conjugate may be stored in the vehicle. Preferred vehicles are sterile solutions, in particular, sterile buffer solutions, such as phosphate buffered saline. Any method of combining the adjuvant and the conjugate in the vehicle such that improved immunological effectiveness of the immunogenic composition is appropriate.

The volume of a single dose of the vaccine of this invention may vary but will be generally within the ranges commonly employed in conventional vaccines. The volume of a single dose is preferably between about 0.1 ml and about 3 ml, preferably between about 0.2 ml and about 1.5 ml, more preferably about 1.0 ml at the concentrations of conjugate and adjuvant noted above.

The vaccine compositions of the invention may be administered by any convenient means.

E. Formulation

Immunogenic conjugates comprising a PPV5B protein(s) or peptide(s) coupled to a carrier molecule can be used as vaccines for immunization against one or more serotypes of PPV5B. The vaccines, comprising the immunogenic conjugate in a physiologically acceptable vehicle, are useful in a method of immunizing animals, preferably swine, for treatment or prevention of infections by PPV5B.

Antibodies generated against immunogenic conjugates of the present invention by immunization with an immunogenic conjugate can be used in passive immunotherapy and generation of antiidiotypic antibodies for treating or preventing infections of PPV5B.

The subject to which the composition is administered is preferably an animal, including but not limited to cows, horses, sheep, pigs, poultry (e.g., chickens), goats, cats, dogs, hamsters, mice and rats; most preferably pigs.

The formulations of the invention comprise an effective immunizing amount of one or more immunogenic compositions or antibodies thereto and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

F. Effective Dose

The compounds described herein can be administered to a subject at therapeutically effective doses to treat PPV5B-associated diseases. The dosage will depend upon the host receiving the vaccine as well as factors such as the size, weight, and age of the host.

The precise amount of immunogenic conjugate or antibody of the invention to be employed in a formulation will depend on the route of administration and the nature of the subject (e.g., species, age, size, stage/level of disease), and should be decided according to the judgment of the practitioner and each subject's circumstances according to standard clinical techniques. An effective immunizing amount is that amount sufficient to treat or prevent a PPV5B infectious disease in a subject. Effective doses may also be extrapolated from dose-response curves derived from animal model test systems and can vary from 0.1 mg/kg to 20 mg/kg, preferably 1 mg/kg to 10 mg/kg.

Immunogenicity of a composition can be determined by monitoring the immune response of test subjects following immunization with the composition by use of any immunoassay known in the art. Generation of a humoral (antibody) response and/or cell-mediated immunity, may be taken as an indication of an immune response. Test subjects may include animals such as pigs, mice, hamsters, dogs, cats, rabbits, cows, horses, sheep, and poultry (e.g. chickens, ducks, geese, and turkeys).

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., quantitative PCR, virus isolation or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutic may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutic can be assessed by measuring the level of the molecule against which the antibody is directed in the animal model subject at suitable time intervals before, during, or after therapy. Any change or absence of change in the amount of the molecule can be identified and correlated with the effect of the treatment on the subject. The level of the molecule can be determined by any method known in the art.

After vaccination of an animal to a PPV5B using the methods and compositions of the present invention, any binding assay known in the art can be used to assess the binding between the resulting antibody and the particular molecule. These assays may also be performed to select antibodies that exhibit a higher affinity or specificity for the particular antigen.

G. Detection and Diagnostic Methods

Antibodies, or binding portions thereof, resulting from the use of native PPV5B, attenuated virus, proteins or peptides of the present invention are useful for detecting in a sample the presence of PPV5B. This detection method comprises the steps of providing an isolated antibody or binding portion thereof raised against a native PPV5B, attenuated virus, protein or peptide of the invention, adding to the isolated antibody or binding portion thereof a sample suspected of containing a quantity of PPV5B virus and detecting the presence of a complex comprising the isolated antibody or binding portion thereof bound to PPV5B virus.

The antibodies or binding portions thereof of the present invention are also useful for detecting in a sample the presence of a PPV5B protein or peptide. This detection method comprises the steps of providing an isolated antibody or binding portion thereof raised against native PPV5B, attenuated virus, protein or peptide, adding to the isolated antibody or binding portion thereof a sample suspected of containing a quantity of the PPV5B protein or peptide, and detecting the presence of a complex comprising the isolated antibody or binding portion thereof bound to the PPV5B protein or peptide.

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby subjects may be tested for aberrant levels of the molecule to which the immunoglobulin binds, and/or for the presence of abnormal forms of such molecules. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In one aspect, an antibody of the invention that immunospecifically binds to a PPV5B native or attenuated virus, protein or peptide may be used to diagnose, prognose or screen for a PPV5B infection.

In another aspect, the invention provides a method of diagnosing or screening for the presence of a PPV5B infection or immunity thereto, comprising measuring in a subject the level of immunospecific binding of an antibody to a sample derived from the subject, in which the antibody immunospecifically binds a PPV5B protein or peptide in which an increase in the level of said immunospecific binding, relative to the level of said immunospecific binding in an analogous sample from a subject not having the infectious disease agent, indicates the presence of PPV5B.

Examples of suitable assays to detect the presence of PPV5B peptides or antagonists thereof include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques wellknown in the art.

The binding activity of a given antibody may be determined according to well known methods. Those skilled in the art will be able to determine operative and optimal assay conditions for each determination by employing routine experimentation.

An additional aspect of the present invention relates to diagnostic kits for the detection or measurement of PPV5B. Kits for diagnostic use are provided, that comprise in one or more containers an anti-PPV5B antibody, and, optionally, a labeled binding partner to the antibody. Alternatively, the anti-PPV5B antibody can be labeled (with a detectable marker, e.g., a chemiluminescent, enzymatic, fluorescent, or radioactive moiety). Accordingly, the present invention provides a diagnostic kit comprising, an anti-PPV5B antibody and a control immunoglobulin. In a specific embodiment, one of the foregoing compounds of the container can be detectably labeled. A kit can optionally further comprise, in a container, a predetermined amount of a PPV5B virus, protein or peptide recognized by the antibody of the kit, for use as a standard or control.

H. Administration to a Subject

Routes of administration include but are not limited to intranasal, oral (e.g., in drinking water), intradermal, and intramuscular. Intramuscular administration is particularly preferred. The skilled artisan will recognize that compositions of the invention may also be administered in one, two or more doses, as well as, by other routes of administration. For example, such other routes include subcutaneously, intracutaneously, intravenously, intravascularly, intraarterially, intraperitnoeally, intrathecally, intratracheally, intracardially, intralobally, intramedullarly, intrapulmonarily, and intravaginally. Depending on the desired duration and effectiveness of the treatment, the compositions according to the invention may be administered once or several times, also intermittently, for instance on a daily basis for several days, weeks or months and in different dosages.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

This application is related to the application filed on Dec. 17, 2012 entitled "Porcine *Parvovirus* 5A, Methods of Use and Vaccine," U.S. Ser. No. 61/738,110, the contents of which are incorporated by reference herein, in its entirety.

EXAMPLES

Materials and Methods

Source of Materials: Tissue homogenates from three pigs were received from an unusual outbreak investigation. The clinical history on the farm was of 200 lb pigs with full body muscle tremors which were present upon rest but exaggerated during movement. Following extensive testing at a veterinary diagnostic laboratory which suggested a viral agent (based on microscopic lesions) but only resulted in the identification of Agent X (a non-classical swine fever virus associated pestivirus), samples were provided to the inventors to help determine the underlying cause of the CNS signs in these animals.

DNA and Protein Analysis: DNA analysis of samples from affected pigs was conducted using high throughput sequencing from 454 Life Sciences (Branford Conn.) ("454 technology"), performed by Operon (Huntsville Ala.). Samples were enriched for viral sequences through nuclease treatment of viral particle protect nucleic acids followed by extraction, random amplification and high throughput sequencing; performed generally as described in Victoria et. al PLoS pathogen 2008 Sep. 26; 4(9):e1000163.

Resultant sequences were initially characterized by BLASTx analysis as divergent members of the Parvoviridae family. Sequences were assembled using Sequencher software and the results of these DNA analyses coupled with targeted sequencing yielded the DNA sequence of SEQ ID NO:1, which is the putative complete coding sequence of the virus denoted as PPV5B. Further analysis of the DNA sequence using Sequencher software resulted in identification of three putative coding regions corresponding to those found in other *parvovirus* species, comprising the viral replicase (SEQ ID NO:2), an open reading frame "ORF3" (SEQ ID NO:3) and the viral capsid protein (SEQ ID NO:4).

Example 1

Identification of a Novel Virus

DNA sequences were identified by 454 technology (viral metagenomics) in samples of lung homogenates of two unrelated pigs from different states. BLASTn and BLASTx analysis revealed the closest identity to porcine parvovirus 4, with a maximum of 67% nucleotide identity in conserved regions of the replicase gene (REP), while the capsid (CAP) coding regions did not exhibit a discernable match at the nucleotide level. At the protein level, the putative replicase protein exhibited ~60% amino acid identity and ~50% identity in the capsid protein. The virus was denoted as a new species, porcine parvovirus 5B (PPV5B). Specific primers were developed based on the capsid coding sequence and PCR based screening of homogenates that were similar in tissue and pathological/clinical characteristics revealed presence of the agent in ~16% of samples. Based on reported clinical signs and virology data associated with the tissues screened, statistically significant association was observed with several other viral agents and clinical pathologies/histopathology.

Example 2

Identification of PPV5B as a Novel Parvovirus and Phylogentic Analysis

Figure 5:
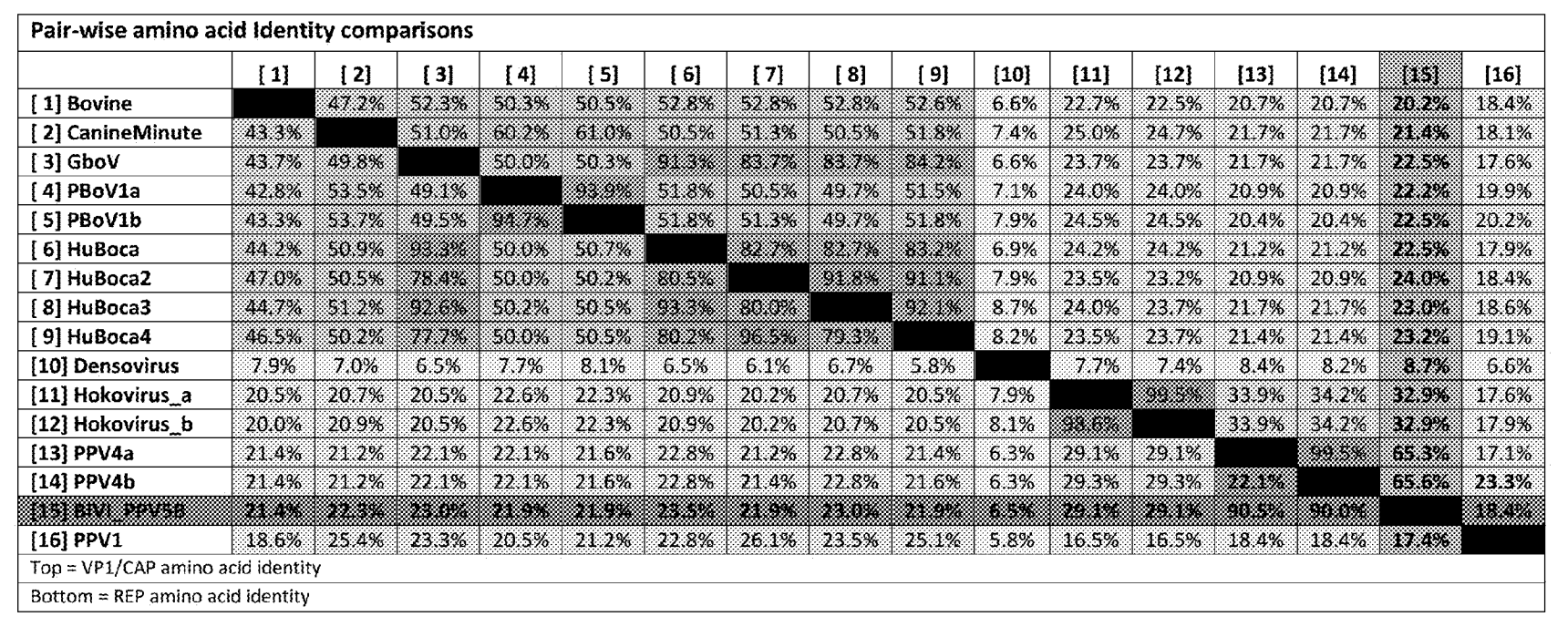

Pair-wise amino acid identities for both the putative replicase (REP) and capsid (VP1/CAP) proteins of multiple known viral species are shown in FIG. 5. PPVSB sequence identity to PPV4, the closest relative, with both REP and CAP (~90%/65%, respectively) supporting designation of PPVSB as a new species.

Phylogenetic analysis (FIG. 6) reveals the virus to be a novel species within the Parvoviridae family and *parvovirus* genus, based on the conserved region of the CAP protein. Similar results are achieved using the more conserved REP protein sequence (not shown).

Example 3

Confirmation of the PPV5B as a Causative Agent of Disease

Brain homogenates from PPVSB-infected CDCD pigs were used to inoculate cesarean-derived-colostrum-deprived (CDCD) animals in an attempt to amplify virus and determine whether co-infection with the novel parvoviruses and PRRSV resulted in increased clinical respiratory signs. In this study, there were an unexpected, high number of mortalities (20-22%) in groups inoculated with the tissue homogenate containing the novel parvoviruses and high titers of PPVSB were identified in serum using PPVSB-specific PCR targeting the capsid coding region. Tissues from one animal in this study were then used to challenge CDCD pigs to reproduce clinical signs. In this study, a systemic infection with high titers of viremia was noted in the majority of infected animals. In groups that received inocula containing PPVSB, there was a high incidence of mortality (20%), lameness, decreased average daily gain, pyrexia, and both macro- and microscopic lesions.

Example 4

Culturing, Isolation and Purification of PPV5B

Small sections of PCR positive tissues (e.g. spleen, brain, lung, intestine etc) are ground up using sterile mortar and pestle. The ground tissue is resuspended in 5-10 ml modified EMEM containing HEPES buffer and antibiotics and clarified to eliminate larger tissue masses. The supernatants are collected and serially passed through various filters to eliminate most of the larger particles including bacteria. Additionally, fecal sample suspension and serum from PCR positive animals are also being processed by serial filtration for virus isolation.

Dilutions of the filtrate are treated with trypsin or left untreated and are adsorbed onto established and primary cell cultures (listed below) in 6-well plates at specific temperatures. The inoculum is aspirated and replaced with 2 ml fresh maintenance medium. The plates are then incubated at 33-37° C. in a 5% $CO_2$ atmosphere and are observed daily for cytopathic effects such as cell rounding, cell-cell fusion, sloughing, cell clustering etc as compared to mock (plain media) inoculated controls. Potential positive wells are screened for virus growth/isolation by PCR.

Established cell lines useful in isolation of virus included: ST (swine testes), SK6 (swine kidney), BHK-21 (baby hamster kidney), VIDO R1 (fetal porcine retina), PK-15 NADC (porcine kidney), PK/WRL (porcine kidney), HRT-180 (human colorectal adenocarcinoma), Hep2 (human epithelial), Vero (African green monkey kidney) and RK-13 (rabbit kidney) among others.

Primary cell cultures useful in the process include: Embryonic porcine lung, kidney, testes, trachea, and intestine cultures, among others.

As the virus is isolated, it is purified by multiple rounds of plaque purification or limiting dilutions and amplified in larger quantities and generate stock cultures for animal experiments.

Example 5

Preparation of a Inactivated Virus and Vaccine

Inactivation is performed between about 35-39° C. and in the presence of 2 to 15 mM BEI, still more preferred in the presence of about 10 mM BEI. Inactivation is performed for at least 24 hours, up to 24 to 72 hours. An equivalent amount of an agent that neutralizes the inactivation agent within the solution is then added; e.g., sodium thiosulfate to an equivalent amount. An inactivated virus preparation is prepared in accordance with methods known in the art, e.g., as disclosed in Preuss, T., et al., Comparison of Two Different Methods for Inactivation of Viruses in Serum, CLINICAL AND DIAGNOSTIC LABORATORY IMMUNOLOGY, (1997), 504-508 or Bahnemann, H. G., Inactivation of viral antigens for vaccine preparation with particular reference to the application of binary ethylenimine, VACCINE, (1990), 299-303. Once an inactivated virus is prepared, the material is combined with a carrier preparation for final vaccine formulation.

Example 6

Preparation of an Attenuated Virus and Vaccine

An attenuated virus preparation is prepared in accordance with methods known in the art, e.g., as disclosed in Vaccine Protocols, 2nd edition; Robinson, Husdon, Cranage, eds, Humana Press 2003. For example, "... wild type viruses are extensively passaged in tissue culture/animal hosts until an acceptable balance is reached between loss of virulence and retention of immunogenicity ..."

Attenuated virus is purified by multiple rounds of plaque purification or limiting dilutions. PCR assays, deep sequencing or immunofluorescence assays are utilized to determine the specificity of the culture material.

An attenuated viral vaccine is prepared by combining a purified attenuated virus preparation with a carrier preparation.

Example 7

Preparation of a Subunit Vaccine Comprising a Capsid Protein

The capsid protein of SEQ ID NO:4 was prepared by expression of the cloned SEQ ID NO:4, or fragments thereof, in various protein expression systems.

Baculovirus Expression: PPV5B capsid protein of SEQ ID NO:4 was expressed in a baculovirus expression system, generally in accordance with the methods disclosed in Kost et al. (6), 2012. The protein was found in low quantity within the insoluble fraction upon initial purification. Methods to increase yield and solubility include, but are not limited to, use of alternative buffer conditions (e.g. urea or guanidine hydrochloride), alternative binding and purification conditions (e.g. cobalt or nickel affinity columns, anion or cation exchange columns), or alternative expression conditions (e.g. temperature, time, alternative cell lines).

Bacterial Expression: PPV5B capsid protein of SEQ ID NO:4 was expressed in a bacterial expression system, generally in accordance with the methods disclosed in EMD Chemicals Inc. Novagen User Protocol TB184. This method included the addition of an inherent HIS-tag contained in the bacterial vector (EMD Chemicals Inc., 2011 (7)) to facilitate purification of the produced protein. Bacterially expressed HIS-tagged capsid protein was purified generally in accordance with the methods disclosed in GE Healthcare, 2012 (8) and resultant products used to generate PPV5B specific antibodies as described in Example 8.

An attenuated subunited vaccine was prepared by combining a purified capsid protein preparation with a carrier preparation.

Example 8

Preparation of Antibodies that Specifically Bind to PPV5B

Antibodies that specifically bind to PPV5B are prepared by immunizing rabbits with antigenic preparations of PPV5B virus, or subunit protein preparations of capsid (SEQ ID NO:4) proteins or fragments thereof. Serum samples from the inoculated rabbits are screened for polyclonal antibodies which bind to the PPV5B antigens. Spleens from inoculated mice which were determined to produce antibodies to the antigen are fused with myeloma cells to produce hybridomas. The hybridomas are then screened for binding to PPV5B antigen.

Polyclonal Antibodies: The HIS-tagged bacterially expressed capsid protein prepared in accordance with Example 7 was used to immunize two New Zealand White rabbits at a custom antibody production service (Rockland Antibodies and Assays; Gilbertsville, Pa.). Rabbits were immunized with approximately 100 µg antigen/rabbit at D0, D7, D14 and D28. For D0 and D7 inoculation, animals were inoculated intradermally; inoculations given at D14 and 28 were administered subcutaneously. Complete Freund's adjuvant was used in the first inoculation; incomplete Freud's adjuvant was used in subsequent inoculations. Serum samples from both rabbits were collected before immunization and at 38 and 45 days post immunization.

Polyclonal antibody preparations were screened for anti-PPV5B specificity by Rockland Antibodies and Assays. Antibodies were produced having binding specificity to purified or partially purified PPV5B protein by immunofluorescent assay (IFA), western blot, and enzyme-linked immunosorbent assay (ELISA). Parameters for specificity of each assay were as follows: western blot specificity were measured by detection of the predicted 79.0 kDa sized protein, IFA specificity measured by comparison to uninfected cells, and ELISA specificity by coating plate with non-relevant protein.

Monoclonal Antibodies: HIS-tagged baculovirus expressed capsid protein prepared in accordance with Example 7 are used to generate monoclonal antibodies in Balb/c mice at a custom antibody production service (Rockland Antibodies and Assays; Gilbertsville, Pa.). Mice are immunized with various PPV5B antigenic preparations according to standard protocols designed by the custom antibody production facility. The immune response following inoculation is monitored by the custom antibody production facility and antibody candidates are selected for generation of hybridomas. Standard protocols for generation of monoclonal antibodies are well known to those in the art, e.g. as disclosed in Gabriele et al. (9), p. 117-135.

Hybridomas are generated by combining B-cell tumor cells cultivated in hybridoma medium to the proliferation phase with spleen cells harvested from inoculated mice determined to produce antibodies to PPV5B antigens according to standard protocols, as disclosed in Gabriele et al. (9), p. 117-135. After fusion and culturing the hybridomas, the hybridomas are screened for binding to PPV5B antigens, and anti-PPV5B producing hybridomas are selected. Monoclonal antibodies produced by hybridomas are purified using affinity chromatography according to standard protocols, as disclosed in Gabriele et al. (9), p. 209-232.

High affinity antibodies specific for PPV5B are identified and further characterized, including determining the epitopes to which they bind, the specificity of the antibody with respect to other related virus species, and suitable high affinity antibodies with high specificity for the PPV5B viral antigen(s) are selected, using immunological techniques well known to the art, e.g. ELISA, Westernblot analysis and epitope mapping (Epitope Mapping Protocols in Methods in Molecular Biology, Vol. 66 (Glenn E. Morris, Ed., 1996) Humana Press, Totowa, N.J.).

Example 9

Diagnostic Assays for PPV5B

ELISA Assay: Antibodies prepared in accordance with Example 8 are used to measure PPV5B in a biological sample using ELISA procedures. The assay is conducted as follows:

Coating antigen selected from the capsid protein of SEQ ID NO:4 is diluted in coating buffer (0.05 M carbonate-bicarbonate buffer; pH 9.6) to achieve a final concentration of 0.25 ng/µl. Plates (High protein binding 96-well ELISA plates Phenix cat no. MPG-655061) are coated with 50 µl/well of coating antigen. Plates are sealed and incubated for 1 hr. at 37° C. or overnight at 4° C. The coating solution is removed and the plate is wash plate three times with 200µl/well PBST (1×PBS+0.05% Tween-20). The plate is coated with 300 µl/well blocking solution (0.5% w/v non-fat dry milk in PBS), sealed and incubated for 1 hr. at 37° C. The blocking solution is removed and the plate is and washed three times with 200μl/well PBST. Samples are diluted 1:100 in blocking solution; 100μl/well of serum samples are added to the plate. Plates are sealed and incubated for 1 hr. at 37° C. Serum samples are removed and the plate is washed three times with 200μl/well PBST. The secondary antibody (HRP-conjugated-goat anti-swine IgG (H+L); Jackson Immuno-Research 114-035-003) is diluted to 1:10,000 in blocking solution and used to coat the plate with 100 μl/well. Plates are sealed and incubated for 1 hr. at 37° C. The secondary antibody is removed and the plate is washed three times with 200 μl/well PBST. Plates are coated with 50 μl/well TMB (3,5,3',5'-tetramethylbenzidine; KPL cat no. 53-00-01). Plates are incubated at room temperature in the dark for approximately ten minutes. Plates are coated with 50 μl/well stop solution (2 M $H_2SO_4$; KPL cat no. 50-85-04). The optical density is read at 450 nm.

PCR Assays: Gel-based PCR and qPCR assays for PPV5B have been optimized. These assays are conducted as follows: For the qPCR assay, each reaction is prepared by adding the following reagents: 10 μl/reaction of 2× SsoFast probe supermix (BioRad, cat no. 172-5233), 5 μl/reaction DEPC-treated water, 1 μl/reaction of the forward primer at a 6 μM concentration (ACC AGA GAA CAG GCG ACA T: SEQ ID NO:6), 1 μl/reaction of the reverse primer at a 6 μM concentration (AAA CAC CTG ATG GGA CCA TAA T: SEQ ID NO:7), 1 μl/reaction of the probe at a 4 μM concentration (6-FAM/ACT CAA CAG CCA GGA CCG AGA ACA CAG GAA/BHQ_1: SEQ ID NO:8) and 2 μl/reaction of extracted DNA. The reaction is performed on a T100 thermal cycler (Bio-Rad) for one cycle at 95° C. for 2 minutes followed by forty cycles at the following two temperatures: 95° C. for 5 seconds followed by 60° C. for 5 seconds. Data is read using a CFX96 optical imaging system (Bio-Rad). For the gel-based assay, each reaction is prepared by adding the following reagents: 12.5 μl/reaction of 2× AmpliTaq Gold Mastermix (Applied Biosystems, cat no. 4302758), 8.0 μl/reaction DEPC-treated water, 1.25 μl/reaction of the forward primer (CCA GAT TTA CAT TTT GAG CAG CTA ACA CAG TAC: SEQ ID NO:9) at a 10 μM concentration, 1.25 μl/reaction of the reverse primer (GGA TAT AAG CCC AAA TCT GAG ACT CTA G: SEQ ID NO:10) at a 10 μM concentration, and 2 μl/reaction of extracted DNA. The reaction is performed on a T100 thermal cycler (Bio-Rad) for one cycle at 95° C. for 5 minutes followed by forty cycles at the following temperatures: 95° C. for 30 seconds, 60° C. for 30 seconds and 72° C. for 45 seconds followed by a final extension at 72° C. for 10 minutes.

Example 10

Evaluation of the Efficacy of PPV5B Vaccine in Pigs

To evaluate the efficacy of the composition of matter that comprises at least one PPV5B protein or polypeptide (prototype PPV5B vaccine) in pigs, a randomized study using five week old colostrum-deprived-cesarean-derived (CDCD) animals randomized into three groups (see Table 2) is performed. Animals are vaccinated with a composition or a placebo (phosphate buffered saline; PBS) at study day 0 (D0) and D14. Animals are challenged on D28 with material known to contain PPV5B. Clinical observations, rectal temperatures, weight measurements and blood collection are monitored. At D56, animals are necropsied to evaluate macroscopic lesions. The efficacy of the PPV5B vaccine is determined by statistically comparing the percent mortality, viremia (titers and duration), seroconversion (titers and duration) and clinical signs between vaccinated and non-vaccinated animals.

TABLE 2

| Group no. | Group | N | Room | Vaccination | Challenge |
| --- | --- | --- | --- | --- | --- |
| 1 | PPV5B-Vx | 10 | 1 and 2 | PPV5B prototype | Yes |
| 2 | PBS-Vx | 10 | 1 and 2 | PBS | Yes |
| 3 | Strict control | 5 | 3 | None | No |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

(1) Cságola A, et al., Detection, prevalence and analysis of emerging porcine *parvovirus* infections. Arch Virol. June; 157(6):1003-10 (2012).

(2) Hijikata M, et al., Identification of new *parvovirus* DNA sequence in swine sera from Myanmar. Jpn J Infect Dis 54:244-245 (2001).

(3) Wang F, et al., Novel *parvovirus* sublineage in the family of Parvoviridae. Virus Genes 41:305-308 (2010).

(4) Lau S K, et al., Identification of novel porcine and bovine parvoviruses closely related to human parvovirus 4. J Gen Virol 89:1840-1848 (2008).

(5) Cheung A K, et al., Identification and molecular cloning of a novel porcine *parvovirus* . Arch Virol 155(5): 801-806 (2010).

(6) Kost et al., Recombinant baculoviruses as mammalian cell gene-delivery vectors, Trends in Biotechnology, 20, 173-180, April 2002. cited by other.

(7) EMD Chemicals Inc. 2011. *Xa/LIC Kits, User Protocol TB*184.

(8) GE Healthcare. *Recombinant Protein Purification Handbook.* 18-1142-75.

(9) Gabriele et al. (eds.), *Antibody Methods and Protocols*, Methods in Molecular Biology, 2012, vol. 901, chapter 7.

What is claimed is:

1. A method of generating an immune response in a mammal, comprising administering an immunologically-effective amount of a porcine parvovirus 5B (PPV5B) comprising an isolated polynucleotide, comprising:
   a) the nucleic acid sequence of SEQ ID NO:1;
   b) a nucleic acid sequence of SEQ ID NO: 1 that encodes a polypeptide of SEQ ID NO:3 or SEQ ID NO:4;
   c) a nucleic acid sequence at least 80% identical to SEQ ID NO:1, which encodes a polypeptide having a biological or immunologically-effective activity of a polypeptide of SEQ ID NO:2, SEQ ID NO:3 or SEQ ID NO:4;
   d) a fragment of the nucleic acid sequence of SEQ ID NO:1, comprising at least 30 contiguous nucleotide sequences encoding SEQ ID NO:4, or
   e) a fragment of the nucleic acid sequence of SEQ ID NO:1, comprising at least 30 contiguous nucleotide sequences of SEQ ID NO:1, and which encode an immunologically-effective activity of an amino acid sequence of SEQ ID NO:3 or SEQ ID NO:4.

2. A method of generating an immune response in a mammal, comprising administering an immunologically-effective amount of a PPV5B, comprising the nucleic acid sequence of SEQ ID NO: 1, which encodes a polypeptide comprising:
   a) the amino acid sequence of SEQ ID NO:3 or SEQ ID NO:4;
   b) an amino acid sequence at least 80% identical to SEQ ID NO:3 or SEQ ID NO:4 and having a biological or immunologically-effective activity of a polypeptide encoded by SEQ ID NO:3 or SEQ ID NO:4;
   c) a fragment of the amino acid sequence of SEQ ID NO:3 or SEQ ID NO:4, comprising at least 13 contiguous amino acids of SEQ ID NO:3 or SEQ ID NO:4;
   d) a fragment of the amino acid sequence of SEQ ID NO:3 or SEQ ID NO:4, comprising at least 13 contiguous amino acids of SEQ ID NO:3 or SEQ ID NO:4, and having an immunologically-effective activity; or
   e) a protein fragment that is encoded by a polynucleotide that comprises at least 39 nucleotides included in the sequences of nucleotides 2161-2860 of SEQ ID NO:1, or nucleotides 2861-5014 of SEQ ID NO:1.

3. A method of generating an immune response in a mammal, comprising administering an immunologically-effective amount of an isolated porcine parvovirus 5B (PPV5B), comprising:
   a) a nucleic acid sequence of SEQ ID NO:1, or
   b) a nucleic acid sequence at least 80% identical to SEQ ID NO:1, which encodes a polypeptide having a biological or immunologically-effective activity of a polypeptide of SEQ ID NO:3 or SEQ ID NO:4.

4. A method of generating an immune response in a mammal, comprising administering an immunologically-effective amount of a killed or attenuated form of a PPV5B according to claim 1.

5. A method of generating an immune response in a mammal, comprising administering an immunologically-effective amount of a killed or attenuated form of a PPV5B according to claim 2.

6. A method of generating an immune response in a mammal, comprising administering an immunologically-effective amount of a killed or attenuated form of a PPV5B according to claim 3.

* * * * *

SEQUENCE LISTING

<160> NUMBER OF SEQ ID NOS: 11

<210> SEQ ID NO 1
<211> LENGTH: 5302
<212> TYPE: DNA
<213> ORGANISM: Porcine parvovirus 5B

<400> SEQUENCE: 1

```
gcttcaagtc tattaatttg cataatttat gcaaagagga agttaacctg attggtcagt      60
tttttggcgg gaagcaattt gattggacgg gaactcaagt cctaatttgc attgacgtgg     120
accaatcaga attgagtaca tattatataa ggaggccgaa aaagaggaag tttgtcattt     180
gcgttttgga gaccatcgcg agcagaactc cgtcgttttc ggcctgtatt tgaagatgga     240
aacctactgg acaggtattt gcagactttt tcctgatgtt ttaaaaatac ctggtgttta     300
tgaaggacgc tatattttg aagttcctgt ttctaccaga gactttatga aatggcctga     360
tatatttcaa aatgaaaaaa ataatgaaaa ctgtgagtct ggcgcggcgc ctgcggcgcc     420
gcgcgatgaa attgacagta atctagtaac ggctgttaga caaggggagg ctctatttag     480
agagcttcaa aaagaactta gaaaatcctg tagattagga gtagatcctg cattttcat      540
gcaattggaa agagttgact caaaaggtgg cttacatttg cattggtgtg tgtctgtgtc     600
cgctggtacc ccgcgagatg ttttaactat attcaaaaat acagaaaaaa agtttcatt     660
atattacttt ggtgttgagg acttagcttt ttttgtgcca cacaaaaata acacggagc      720
atggaaaagc acagatgaag ggtttattta taattatttg ctaaaaaaac taccactgaa     780
agaatgtctt tatgcatgga ctacaattgg aggtacaata ggtgaagcct gtttaaatac     840
agaaaaaaga aaagaactat tagataatag acaagatcca gcagttattg aagaattatc     900
tgctcccatg tacaaatgtg ccactggaga aaaaatgcta gacattgtac agtggttggt     960
agacaataat atttgttctg aatccagatg ggagggaaaa aatgctctaa gcttatactc    1020
attcttagcc acacaagctg aggatatat ggcaaaacaa tgcttgagaa tcgctcagca    1080
aaaattacta aagaaaaaat cactagggtt aaccttaatg gatttaaaa acatggatgc    1140
tttaagagct ttccaacaaa gtgacatgga gtgctcattc gatcataaca gaatacatta    1200
cattttgca gctaacaact atgatcctaa aattgctgca gttataatgt ttcactggag    1260
catgaaacaa acgggaaaaa gaaactgtgt atggttttac ggtcctgcta acaggaaaa     1320
aacaaatatt gcacaggcaa tctgccatag ctcagctaat tatggcaatg ttaactggaa    1380
caatccaaat tttcctttc aagatattgt aggagctcag gtagggtggt gggaagaagg    1440
gaaaatgaca ggagacatgg tagaagctgc aaaagctttg ctgggggaa ctgctttgcg     1500
catcgaccgc aaatgtatgc aatctgttga agtcaacagt ccaccgttta ttataacatc    1560
gaatgtggac atgaccgtgg ttcaagaagg aagttttgta agctttgaac caacagcc      1620
gttagaggac aggatgataa aatttcatt taacctgaca ctacctggaa actttggtct    1680
gattacaact gaagaagtga atcttttttt ccggatgggt gcaaaacttt cagttaaacc    1740
tgaaatcatg aattgccaaa ttttcaaaag gaacctgcc agcatccgcc acctagttcc    1800
tcttggagaa attcctccac caaaggagat gcataaaaaa cgacagccac tctatttgag    1860
agctgaacca gatgaagaac aagaaacacc agacgtcttg gatcattggt ttgaagaacc    1920
aagtcaaaaa agaaagaaga cagaagaccc tgcaaacacg acacctcctg cggcttatga    1980
gaatttagat gacaactttg aacctgttcc aggtaagaat tttgcattta tcatttttt     2040
atgttccaaa acaatagagc aaactggtga tatgtgcata attcttacag atagccaagt    2100
```

```
gaacctgata tttgacgtgg tctacgaaga gacaccagag gtggacgaag tggaggaaca    2160
atgagcttta gtgggtattc taaaaatctc cccccgggtt tagaggaagt tacattccca    2220 tttttgggttg attttttgct tgccagaata gctgatttta ttaattggtg tgggtattat    2280
aatattaaat gtccagaagc agaaaaggta tttagtattg gacaatctac acaggtttta    2340
cttaaatggc cgggtgcaca gggaaaagaa aaccgagtta agaactttac cgaagctgcg    2400
tttccatata tgaaagtacc tgtgagacca gacaacattg aatggattaa aatccatgag    2460
atgctacata attatgatag acaaataaca ccgcagacaa ctgagaatga tttacttgca    2520
gctatcactg ctgacttcga tcagagagag atcatccatc cagtcaccgg cgagaaatgg    2580
gttttcggta agaaaacaga agcttttgct actgatttgg aagaagccgt ggatgaagaa    2640
gatcctgata cagagaaaaa acaacctact gataaaacac aaagtaataa caagaaaggg    2700
gaaattggtg aaaagaaaga agaaggtgat acccttacgt caaatgagga acatcaccaa    2760
tcaagaaaac tattagaaca cgactcaagc gaagaacaac cagaagaagc tggtcaccga    2820
gaacagaaag aactagaaga caatattgaa gacatcaaac atggagcggg agaagaccaa    2880
accggaaccg gtatcaactg gccaggacat cgctacacag gtcctggaaa tccactccct    2940
cacggagctc ctcgcaatga aattgatctc tctgctgcga acatgatat caggtacaaa    3000 caatattctc gatatggtca ctggccatac atttgggcgc catatattga taaaaaaatg    3060
caagaagata ttagagagat agtaaaaaaa ggtttaggat tagaaggtaa acttttaggt    3120
aaccttatat cagctttatg gcaagcaaaa tacagattag gagccccgat atatgaaatt    3180
ttaaaaacaa ttttaccccc gaaaagtatg cctactaaag aatctgtaga aaaacattta    3240
ccaaaacctt tgcccattga tcctccacag acatccttac caggtgcatc tcctcctcga    3300
actcctgact tgggtggcga gactggaatg aatgaagagc ctccagcaaa aagaagaatg    3360
acagaagaca gatgtgacag caccacaagg tgcgaaacat tggacacaca atatgaggat    3420
tctaaaatgg cgggaggggg tggggggga gggaatcaac ctaaaagttc ttggattggg    3480
ggggctttct ttactgatac gacggttact acttatggta ctagaaggtg tgtgcttagc    3540
tcttttccgc ataactactg caccacagag agcggggatc atataccag ccttgttgtc    3600 tgtactccat ggtactatta tgatcttaac attctatcag ctcatttctc tccctctgct    3660
tggcaaacgc ttttagaaga gtatgatgct tttaaacctt taaaattgga agttaaaatt    3720
aaagagatag ttgttaaaga tgttaataat atgacaggga acaatgctg tgacacagtt    3780 tctgacaatg ccatggctgc agtgctgtgt tttgaggata cacattacga gctgccatat    3840
gttttgggag ggggacagct aacagtgcct ggtcatcttc caggacaaac ttatgaactt    3900
ccaaaatact gctatagaac tgtgggaaaa ccgcatagcg agatgtggtc acctgtagat    3960
ggttccaaaa gagcccactt agacatgcct tttgttcagc caacacagaa cactgagttc    4020
tttattttag agaacagaca ctctaccatc cttcacacag gcaatgaatt ctttcaaacc    4080
tatgactttc cagatttaca ttttgagcag ctaacacagt acatgtggga cgcgaggaga    4140
cttgacaatc caatgaaagg tcaagaata caggttatga aaaacaaacc tacagaaaac    4200
aaagatcaaa tgtttggtat cagagcttcg agttacctcg ttccctggat tgtcaactct    4260
ctaaacagac ctgctatgtt tttacaagga ggaagattaa aagacgggga ttattccatt    4320
gttgggcctg ggaccagaga acaggcgaca taccactact ttaatgatac acctgtcgtg    4380
gttgaaagag atatttacaa atttacaact agtatgctta aaagagaaac tcaacagcca    4440
```

```
ggaccgagaa cacaggaaac aacggtaaaa acacctgatg ggaccataat tataacaact    4500
aacagtttag cgtatggaca ggtgcctgaa acattgata acataccgag tgatcacaaa    4560
gccgctttcg gggttacagg gtacaggctt gctgtcgctg aacagagagg gtatagcaca    4620
cctggaatgc cttctcatat aagggagata ttattgacaa aaacaccgaa actattagaa    4680
aaagatcagc aagaaatcac atttccaaac tttgaagggt ctgtcagcga aaaaacttcc    4740
gctaatctag agtctcagat ttgggcttat atccctaaca ctgataacaa acataactgc    4800
ggaacgcccc ctttatctat atggggaatg gaaaatcctc cacctatggt tttttttgagg    4860 ttactccctc aactgggacc ccctgaaaaa tccagctgtt ctggaagcaa accttctaaa    4920
aagttcttga atcagtactg ccaatttttta ctggaatata ctgtaacatg ggctgttgtg    4980
aggcgaaaga acatactcc gaggtggaac cctatgccgg gggtcacaat tccaacttat    5040
aacaacgatc ctgtgtacat ccttgaccaa aatggatttt ataaattgcc agaaactgtt    5100
tggacagcaa agcaacgtgt tagagcgcga agataataaa aaaaaatttg agaaaaaaaa    5160
agttacttcc tcttttttt tgaatttgaa aagcgccagg cctctcgccg gtcgcccctg    5220
acgtcacatc cgcttccggg tcaagggcg gggtcaaagg tcaaaggtct tcatacgtca    5280
tatccgcttc cgggtcatga cc                                              5302
```

<210> SEQ ID NO 2
<211> LENGTH: 601
<212> TYPE: PRT
<213> ORGANISM: Porcine parvovirus 5B

<400> SEQUENCE: 2

```
Met Glu Thr Tyr Trp Thr Gly Ile Cys Arg Leu Phe Pro Asp Val Leu
 1               5                  10                  15

Lys Ile Pro Gly Val Tyr Glu Gly Arg Tyr Ile Phe Glu Val Pro Val
             20                  25                  30

Ser Thr Arg Asp Phe Met Lys Trp Pro Asp Ile Phe Gln Asn Glu Lys
         35                  40                  45

Asn Asn Glu Asn Cys Glu Ser Gly Ala Ala Pro Ala Ala Pro Arg Asp
     50                  55                  60

Glu Ile Asp Ser Asn Leu Val Thr Ala Val Arg Gln Gly Glu Ala Leu
 65                  70                  75                  80

Phe Arg Glu Leu Gln Lys Glu Leu Arg Lys Ser Cys Arg Leu Gly Val
                 85                  90                  95

Asp Pro Gly Ile Phe Met Gln Leu Glu Arg Val Asp Ser Lys Gly Gly
            100                 105                 110

Leu His Leu His Trp Cys Val Ser Val Ser Ala Gly Thr Pro Arg Asp
        115                 120                 125

Val Leu Thr Ile Phe Lys Asn Thr Glu Lys Lys Val Ser Leu Tyr Tyr
    130                 135                 140

Phe Gly Val Glu Gly Leu Ser Phe Phe Val Pro His Lys Asn Lys His
145                 150                 155                 160

Gly Ala Trp Lys Ser Thr Asp Glu Gly Phe Ile Tyr Asn Tyr Leu Leu
                165                 170                 175

Lys Lys Leu Pro Leu Lys Glu Cys Leu Tyr Ala Trp Thr Thr Ile Gly
            180                 185                 190

Gly Thr Ile Gly Glu Ala Cys Leu Asn Thr Glu Lys Arg Lys Glu Leu
        195                 200                 205

Leu Asp Asn Arg Gln Asp Pro Ala Val Ile Glu Glu Leu Ser Ala Pro
    210                 215                 220
```

Met Tyr Lys Cys Ala Thr Gly Glu Lys Met Leu Asp Ile Val Gln Trp
225                 230                 235                 240

Leu Val Asp Asn Asn Ile Cys Ser Glu Ser Arg Trp Glu Gly Lys Asn
            245                 250                 255

Ala Leu Ser Leu Tyr Ser Phe Leu Ala Thr Gln Ala Gly Gly Tyr Met
            260                 265                 270

Ala Lys Gln Cys Leu Arg Ile Ala Gln Gln Lys Leu Leu Lys Glu Lys
            275                 280                 285

Ser Leu Gly Leu Thr Leu Met Asp Phe Lys Asn Met Asp Ala Leu Arg
290                 295                 300

Ala Phe Gln Gln Ser Asp Met Glu Cys Ser Phe Asp His Asn Arg Ile
305                 310                 315                 320

His Tyr Ile Phe Ala Ala Asn Asn Tyr Asp Pro Lys Ile Ala Ala Val
            325                 330                 335

Ile Met Phe His Trp Ser Met Lys Gln Thr Gly Lys Arg Asn Cys Val
            340                 345                 350

Trp Phe Tyr Gly Pro Ala Thr Thr Gly Lys Thr Asn Ile Ala Gln Ala
            355                 360                 365

Ile Cys His Ser Ser Ala Asn Tyr Gly Asn Val Asn Trp Asn Asn Pro
370                 375                 380

Asn Phe Pro Phe Gln Asp Ile Val Gly Ala Gln Val Gly Trp Trp Glu
385                 390                 395                 400

Glu Gly Lys Met Thr Gly Asp Met Val Glu Ala Ala Lys Ala Leu Leu
            405                 410                 415

Gly Gly Thr Ala Leu Arg Ile Asp Arg Lys Cys Met Gln Ser Val Glu
            420                 425                 430

Val Asn Ser Pro Pro Phe Ile Ile Thr Ser Asn Val Asp Met Thr Val
435                 440                 445

Val Gln Glu Gly Ser Phe Val Ser Phe Glu His Gln Gln Pro Leu Glu
450                 455                 460

Asp Arg Met Ile Lys Phe Ser Phe Asn Leu Thr Leu Pro Gly Asn Phe
465                 470                 475                 480

Gly Leu Ile Thr Thr Glu Glu Val Lys Ser Phe Phe Arg Met Gly Ala
            485                 490                 495

Lys Leu Ser Val Lys Pro Glu Ile Met Asn Cys Gln Ile Phe Lys Arg
            500                 505                 510

Gly Pro Ala Ser Ile Arg His Leu Val Pro Leu Gly Glu Ile Pro Pro
            515                 520                 525

Pro Lys Glu Met His Lys Lys Arg Gln Pro Leu Tyr Leu Arg Ala Glu
            530                 535                 540

Pro Asp Glu Glu Gln Glu Thr Pro Asp Val Leu Asp His Trp Phe Glu
545                 550                 555                 560

Glu Pro Ser Gln Lys Arg Lys Lys Thr Glu Asp Pro Ala Asn Thr Thr
            565                 570                 575

Pro Pro Ala Ala Tyr Glu Asn Leu Asp Asp Asn Phe Glu Pro Val Pro
            580                 585                 590

Gly Lys Asn Phe Ala Phe Ile Ile Phe
            595                 600

<210> SEQ ID NO 3
<211> LENGTH: 233
<212> TYPE: PRT
<213> ORGANISM: Porcine parvovirus 5B

<400> SEQUENCE: 3

```
Met Ser Phe Ser Gly Tyr Ser Lys Asn Leu Pro Pro Gly Leu Glu Glu
1               5                   10                  15

Val Thr Phe Pro Phe Trp Val Asp Phe Leu Leu Ala Arg Ile Ala Asp
            20                  25                  30

Phe Ile Asn Trp Cys Gly Tyr Tyr Asn Ile Lys Cys Pro Glu Ala Glu
        35                  40                  45

Lys Val Phe Ser Ile Gly Gln Ser Thr Gln Val Leu Leu Lys Trp Pro
    50                  55                  60

Gly Ala Gln Gly Lys Glu Asn Arg Val Lys Asn Phe Thr Glu Ala Ala
65                  70                  75                  80

Phe Pro Tyr Met Lys Val Pro Val Arg Pro Asp Asn Ile Glu Trp Ile
                85                  90                  95

Lys Ile His Glu Met Leu His Asn Tyr Asp Arg Gln Ile Thr Pro Gln
            100                 105                 110

Thr Thr Glu Asn Asp Leu Leu Ala Ala Ile Thr Ala Asp Phe Asp Gln
        115                 120                 125

Arg Glu Ile Ile His Pro Val Thr Gly Glu Lys Trp Val Phe Gly Lys
    130                 135                 140

Lys Thr Glu Ala Phe Ala Thr Asp Leu Glu Glu Ala Val Asp Glu Glu
145                 150                 155                 160

Asp Pro Asp Thr Glu Lys Lys Gln Pro Thr Asp Lys Thr Gln Ser Asn
                165                 170                 175

Asn Lys Lys Gly Glu Ile Gly Glu Lys Lys Glu Glu Gly Asp Thr Leu
            180                 185                 190

Thr Ser Asn Glu Glu His His Gln Ser Arg Lys Leu Leu Glu His Asp
        195                 200                 205

Ser Ser Glu Glu Gln Pro Glu Glu Ala Gly His Arg Glu Gln Lys Glu
    210                 215                 220

Leu Glu Asp Asn Ile Glu Asp Ile Lys
225                 230
```

<210> SEQ ID NO 4
<211> LENGTH: 891
<212> TYPE: PRT
<213> ORGANISM: Porcine parvovirus 5B

<400> SEQUENCE: 4

```
Met Leu His Asn Tyr Asp Arg Gln Ile Thr Pro Gln Thr Thr Glu Asn
1               5                   10                  15

Asp Leu Leu Ala Ala Ile Thr Ala Asp Phe Asp Gln Arg Glu Ile Ile
            20                  25                  30

His Pro Val Thr Gly Glu Lys Trp Val Phe Gly Lys Lys Thr Glu Ala
        35                  40                  45

Phe Ala Thr Asp Leu Glu Glu Ala Val Asp Glu Glu Asp Pro Asp Thr
    50                  55                  60

Glu Lys Lys Gln Pro Thr Asp Lys Thr Gln Ser Asn Asn Lys Lys Gly
65                  70                  75                  80

Glu Ile Gly Glu Lys Lys Glu Glu Gly Asp Thr Leu Thr Ser Asn Glu
                85                  90                  95

Glu His His Gln Ser Arg Lys Leu Leu Glu His Asp Ser Ser Glu Glu
            100                 105                 110

Gln Pro Glu Glu Ala Gly His Arg Glu Gln Lys Glu Leu Glu Asp Asn
        115                 120                 125
```

```
Ile Glu Asp Ile Lys His Gly Ala Gly Glu Asp Gln Thr Gly Thr Gly
    130                 135                 140
Ile Asn Trp Pro Gly His Arg Tyr Thr Gly Pro Gly Asn Pro Leu Pro
145                 150                 155                 160
His Gly Ala Pro Arg Asn Glu Ile Asp Leu Ser Ala Ala Lys His Asp
                165                 170                 175
Ile Arg Tyr Lys Gln Tyr Ser Arg Tyr Gly His Trp Pro Tyr Ile Trp
            180                 185                 190
Ala Pro Tyr Ile Asp Lys Lys Met Gln Glu Asp Ile Arg Glu Ile Val
        195                 200                 205
Lys Lys Gly Leu Gly Leu Glu Gly Lys Leu Leu Gly Asn Leu Ile Ser
210                 215                 220
Ala Leu Trp Gln Ala Lys Tyr Arg Leu Gly Ala Pro Ile Tyr Glu Ile
225                 230                 235                 240
Leu Lys Thr Ile Leu Pro Pro Lys Ser Met Pro Thr Lys Glu Ser Val
                245                 250                 255
Glu Lys His Leu Pro Lys Pro Leu Pro Ile Asp Pro Gln Thr Ser
            260                 265                 270
Leu Pro Gly Ala Ser Pro Pro Arg Thr Pro Asp Leu Gly Gly Glu Thr
        275                 280                 285
Gly Met Asn Glu Glu Pro Pro Ala Lys Arg Arg Met Thr Glu Asp Arg
    290                 295                 300
Cys Asp Ser Thr Thr Arg Cys Glu Thr Leu Asp Thr Gln Tyr Glu Asp
305                 310                 315                 320
Ser Lys Met Ala Gly Gly Gly Gly Gly Asn Gln Pro Lys Ser
                325                 330                 335
Ser Trp Ile Gly Gly Ala Phe Phe Thr Asp Thr Thr Val Thr Thr Tyr
            340                 345                 350
Gly Thr Arg Arg Cys Val Leu Ser Ser Phe Pro His Asn Tyr Cys Thr
        355                 360                 365
Thr Glu Ser Gly Asp His Ile Pro Ser Leu Val Val Cys Thr Pro Trp
    370                 375                 380
Tyr Tyr Tyr Asp Leu Asn Ile Leu Ser Ala His Phe Ser Pro Ser Ala
385                 390                 395                 400
Trp Gln Thr Leu Leu Glu Glu Tyr Asp Ala Phe Lys Pro Leu Lys Leu
                405                 410                 415
Glu Val Lys Ile Lys Glu Ile Val Val Lys Asp Val Asn Asn Met Thr
            420                 425                 430
Gly Lys Gln Cys Cys Asp Thr Val Ser Asp Asn Ala Met Ala Ala Val
        435                 440                 445
Leu Cys Phe Glu Asp Thr His Tyr Glu Leu Pro Tyr Val Leu Gly Gly
    450                 455                 460
Gly Gln Leu Thr Val Pro Gly His Leu Pro Gly Gln Thr Tyr Glu Leu
465                 470                 475                 480
Pro Lys Tyr Cys Tyr Arg Thr Val Gly Lys Pro His Ser Glu Met Trp
                485                 490                 495
Ser Pro Val Asp Gly Ser Lys Arg Ala His Leu Asp Met Pro Phe Val
            500                 505                 510
Gln Pro Thr Gln Asn Thr Glu Phe Phe Ile Leu Glu Asn Arg His Ser
        515                 520                 525
Thr Ile Leu His Thr Gly Asn Glu Phe Phe Gln Thr Tyr Asp Phe Pro
    530                 535                 540
Asp Leu His Phe Glu Gln Leu Thr Gln Tyr Met Trp Asp Ala Arg Arg
```

-continued

```
545                 550                 555                 560

Leu Asp Asn Pro Met Lys Gly Gln Arg Ile Gln Val Met Lys Asn Lys
                565                 570                 575

Pro Thr Glu Asn Lys Asp Gln Met Phe Gly Ile Arg Ala Ser Ser Tyr
            580                 585                 590

Leu Val Pro Trp Ile Val Asn Ser Leu Asn Arg Pro Ala Met Phe Leu
        595                 600                 605

Gln Gly Gly Arg Leu Lys Asp Gly Asp Tyr Ser Ile Val Gly Pro Gly
    610                 615                 620

Thr Arg Glu Gln Ala Thr Tyr His Tyr Phe Asn Asp Thr Pro Val Val
625                 630                 635                 640

Val Glu Arg Asp Ile Tyr Lys Phe Thr Thr Ser Met Leu Lys Arg Glu
                645                 650                 655

Thr Gln Gln Pro Gly Pro Arg Thr Gln Glu Thr Thr Val Lys Thr Pro
            660                 665                 670

Asp Gly Thr Ile Ile Ile Thr Thr Asn Ser Leu Ala Tyr Gly Gln Val
        675                 680                 685

Pro Glu Asn Ile Asp Asn Ile Pro Ser Asp His Lys Ala Ala Phe Gly
    690                 695                 700

Val Thr Gly Tyr Arg Leu Ala Val Ala Glu Gln Arg Gly Tyr Ser Thr
705                 710                 715                 720

Pro Gly Met Pro Ser His Ile Arg Glu Ile Leu Leu Thr Lys Thr Pro
                725                 730                 735

Lys Leu Leu Glu Lys Asp Gln Gln Ile Thr Phe Pro Asn Phe Glu
            740                 745                 750

Gly Ser Val Ser Glu Lys Thr Ser Ala Asn Leu Glu Ser Gln Ile Trp
        755                 760                 765

Ala Tyr Ile Pro Asn Thr Asp Asn Lys His Asn Cys Gly Thr Pro Pro
    770                 775                 780

Leu Ser Ile Trp Gly Met Glu Asn Pro Pro Met Val Phe Leu Arg
785                 790                 795                 800

Leu Leu Pro Gln Leu Gly Pro Pro Glu Lys Ser Ser Cys Ser Gly Ser
                805                 810                 815

Lys Pro Ser Lys Lys Phe Leu Asn Gln Tyr Cys Gln Phe Leu Leu Glu
            820                 825                 830

Tyr Thr Val Thr Trp Ala Val Val Arg Arg Lys Lys His Thr Pro Arg
        835                 840                 845

Trp Asn Pro Met Pro Gly Val Thr Ile Pro Thr Tyr Asn Asn Asp Pro
    850                 855                 860

Val Tyr Ile Leu Asp Gln Asn Gly Phe Tyr Lys Leu Pro Glu Thr Val
865                 870                 875                 880

Trp Thr Ala Lys Gln Arg Val Arg Ala Arg Arg
                885                 890

<210> SEQ ID NO 5
<211> LENGTH: 685
<212> TYPE: PRT
<213> ORGANISM: Porcine parvovirus 4

<400> SEQUENCE: 5

Lys His Gly His Trp Pro His Leu Trp Ala Pro Phe Val Asp Arg Gln
1               5                   10                  15

Met Ser Gln Glu Ile Gln Gln Val Leu Lys Gly Ser Thr Lys Leu Ser
            20                  25                  30
```

-continued

```
Gln Lys Leu Leu Ala Asn Phe Ile Ile Ala Leu Trp Arg Ala Lys Glu
             35                  40                  45

Lys Ile Gly Ala Pro Ile Tyr Glu Ile Val Lys Gly Val Phe Pro Ser
 50                  55                  60

Val Asp Lys Lys Thr Val Glu Ser Leu Leu Pro His Pro Asp Pro Ile
 65                  70                  75                  80

Pro Ala Pro Pro Ser Ser Pro Gln Arg Gly Ser Lys Arg Ala Ser Pro
                 85                  90                  95

Pro Gln Ser Pro Asn Ala His Asp Glu Asp Thr Met Ser Gly His Lys
            100                 105                 110

Arg Gln Lys Thr Met Glu Val Glu Ser Glu Cys Asp Lys Ser Leu Leu
            115                 120                 125

Cys Pro Thr Gln Asn Ala Gly Ala Asp Phe Glu Leu Cys Gly Thr Gly
        130                 135                 140

Gly Gly Ala Thr Asn Glu Lys Gly Thr Trp Val Gly Gly Thr Gln Phe
145                 150                 155                 160

Thr Asp Thr Ser Ile Arg Thr Phe Gly Thr Arg Arg Cys Val Leu Ser
                165                 170                 175

Ala Phe Pro Asp Thr Tyr Cys Ser Met Met Ser Gly Asp Ala Ile Pro
            180                 185                 190

Ser Ile Ile Phe Asn Thr Pro Trp Tyr Tyr Tyr Asp Leu Asn Ile Met
        195                 200                 205

Ser Cys His Phe Ser Pro Ser Ala Phe Gln Thr Leu Ile Glu Asp Tyr
    210                 215                 220

Asp Ala Phe Arg Pro Arg Ser Leu Thr Val His Leu Lys Glu Leu Val
225                 230                 235                 240

Ile Lys Asp Val Cys Gln Gln Gln Gly Leu Gln Ala Glu Gln Val Ser
                245                 250                 255

Asp Asn Asn Ser Ala Thr Leu Leu Ala Phe Glu Asp Val Asn Tyr Glu
            260                 265                 270

Leu Pro Tyr Val Leu Gly Gly Gln Val Ser Val Pro Gly His Leu
        275                 280                 285

Pro Gly Gln Pro Tyr Gln Leu Pro Lys Tyr Ser Tyr Arg Thr Val Gly
    290                 295                 300

Lys Pro Asp Pro Asn Ser Gly Phe Val Pro Gly Arg Asn Thr His Pro
305                 310                 315                 320

Asp Gln Gly Pro Gly His Pro Lys Ala Ser Lys Thr Ile Trp Tyr Ser
                325                 330                 335

Gln Tyr Leu Glu Thr Gln Asp Thr Glu Phe Tyr Ile Leu Glu Asn His
            340                 345                 350

Lys Ala Thr Ile Leu His Ser Gly Asn Thr Phe Ser Gln Asn Tyr Asn
        355                 360                 365

Phe Pro Asp Leu Pro Phe Glu Gln Leu Thr Gln Tyr Met Trp Asp Ala
    370                 375                 380

Arg Arg Gln Asp Asn Pro Leu Ile Asp Gln Arg Ile Gln Val Met Ser
385                 390                 395                 400

Arg Met Tyr Asp Asp Gly Pro Gln Lys Thr Phe Ala Ile Lys Val Asn
                405                 410                 415

Pro Tyr Ile Val Pro Phe Thr Val Lys Ser Thr Ser Arg Pro Ala Met
            420                 425                 430

Phe Leu Ala Gly Gly Arg Phe Lys Asp Gly Asp Tyr Ser Ile Thr Gly
        435                 440                 445

Pro Gly Asp Arg Glu Lys Thr Ser Phe Arg Tyr Tyr Asn Asp Pro Pro
```

```
                450              455              460
Trp Ile Ile Thr Arg Asp Thr Tyr Leu Phe Ser Ser Asp Leu Ala Lys
465                  470                  475                  480

Thr Glu Arg Glu Gln Pro Gly Pro Arg Gln Gly Asp Thr Val Val Arg
                485                  490                  495

Thr Pro Asp Gly Thr Leu Ile Val Thr Thr Asn Ala Leu Ala Tyr Gly
                500                  505                  510

Tyr Thr Thr Glu Tyr Leu Lys Asn Ile Pro Leu Leu Ser Ser Lys Tyr
                515                  520                  525

His Gly Val Glu Asn Phe Arg Leu Ala Val Glu Asn Glu Arg Gly Tyr
                530                  535                  540

Ser Met Pro Gly His Pro Ser His Ile Arg Glu Thr Leu Phe Arg Gly
545                  550                  555                  560

Lys Leu Pro Ser Glu Ile Arg Glu Ser Thr Ile Lys Ser Glu Asp Gln
                565                  570                  575

Arg Lys Glu Ile Thr Phe Pro Asp Tyr Met Gly Ser Val Asn Glu Lys
                580                  585                  590

Thr Thr Ala Asn Leu Glu Ser Gln Ile Trp Ser Gln Ile Pro Asn Thr
                595                  600                  605

Asp Ile Thr Glu Lys Cys Thr Thr Pro Pro Leu Ser Ile Trp Gly Met
                610                  615                  620

Lys Asn Pro Pro Met Val Phe Leu Arg Leu Leu Ala Gln Met Gly
625                  630                  635                  640

Pro Pro Arg Arg Ser Ala Cys Ser Gly Ser Ile Pro Ser Asn Thr Tyr
                645                  650                  655

Leu Asn Gln Tyr Cys Gln Phe Leu Leu Thr Tyr Glu Met Glu Trp Asp
                660                  665                  670

Val Ile Lys Arg Thr Arg Lys Thr Val Arg Trp Asn Pro
                675                  680                  685

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accagagaac aggcgacat                                                19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaacacctga tgggaccata at                                            22

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 8
actcaacagc caggaccgag aacacaggaa                                      30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagatttac attttgagca gctaacacag tac                                  33

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatataagc ccaaatctga gactctag                                        28

<210> SEQ ID NO 11
<211> LENGTH: 597
<212> TYPE: PRT
<213> ORGANISM: Porcine parvovirus 4

<400> SEQUENCE: 11
```

Met Glu Thr Tyr Trp Thr Gly Ile Cys Arg Leu Phe Pro Asp Val Leu
1               5                   10                  15

Lys Ile Pro Gly Val Tyr Glu Gly Arg Tyr Ile Phe Glu Val Pro Ile
            20                  25                  30

Ser Thr Arg Asp Cys Met Lys Trp Pro Asp Ile Phe Gly Asn Glu Asn
        35                  40                  45

Asn Ser Glu Asn Gln Gln Ser Gly Ala Ala Pro Ala Ala Pro Arg Glu
    50                  55                  60

Asn Leu Asn Ser Asn Leu Val Ile Ala Val Arg Gln Ala Glu Ala Leu
65                  70                  75                  80

Phe Arg Glu Leu Gln Lys Glu Leu Arg Lys Ser Cys Arg Leu Gly Val
                85                  90                  95

Asp Pro Gly Ile Phe Met Gln Leu Glu Glu Val Asp Ser Lys Gly Gly
            100                 105                 110

Leu His Leu His Trp Cys Val Ser Val Ser Ala Gly Thr Pro Arg Asp
        115                 120                 125

Val Leu Thr Ile Phe Lys Asn Thr Glu Lys Lys Val Ser Leu Tyr Tyr
    130                 135                 140

Phe Gly Val Glu Gly Leu Ser Phe Phe Val Pro His Lys Asn Lys His
145                 150                 155                 160

Gly Ala Trp Lys Ser Thr Asp Glu Gly Phe Ile Tyr Asn Tyr Leu Leu
                165                 170                 175

Lys Lys Leu Pro Leu Lys Glu Cys Leu Tyr Ala Trp Thr Thr Ile Gly
            180                 185                 190

Gly Ala Ile Gly Asp Ala Cys Leu Asn Thr Lys Arg Lys Glu Leu
        195                 200                 205

Leu Asp Asn Arg Gln Asp Pro Ala Val Ile Glu Glu Leu Ser Ala Pro
    210                 215                 220

```
Met Tyr Lys Cys Ala Thr Gly Glu Lys Met Leu Asp Ile Val Gln Trp
225                 230                 235                 240

Leu Val Asp Asn Asn Ile Cys Ser Glu Ser Arg Trp Glu Asn Lys Asn
            245                 250                 255

Ala Leu Ser Leu Tyr Ser Phe Leu Ala Thr Gln Ala Gly Tyr Met
        260                 265                 270

Ala Lys Gln Cys Leu Arg Ile Ala Gln Gln Lys Leu Leu Lys Glu Lys
            275                 280                 285

Pro Leu Gly Leu Thr Leu Met Glu Phe Lys Asp Met Asn Ala Leu Arg
        290                 295                 300

Arg Phe Gln Gln Asp Glu Gly Glu Met Thr Phe Asp Asn Asn Arg Met
305                 310                 315                 320

His Tyr Ile Phe Ala Ile Asn Asn Tyr Asp Pro Lys Ile Ala Ser Val
                325                 330                 335

Ile Met Tyr Phe Trp Ser Met Lys Gln Thr Gly Lys Arg Asn Cys Val
            340                 345                 350

Trp Phe Tyr Gly Pro Ala Thr Thr Gly Lys Thr Asn Met Ala Gln Ala
        355                 360                 365

Ile Cys His Ser Ser Ala Asn Tyr Gly Asn Val Asn Trp Asn Asn Ala
370                 375                 380

Asn Phe Pro Phe Gln Asp Ile Val Gly Ala Gln Val Gly Trp Trp Glu
385                 390                 395                 400

Glu Gly Lys Met Thr Gly Asp Met Val Glu Ala Ala Lys Ala Leu Leu
                405                 410                 415

Gly Gly Thr Ala Leu Arg Ile Asp Arg Lys Cys Met Gln Ser Ile Glu
            420                 425                 430

Val Asn Ser Pro Pro Phe Leu Ile Thr Ser Asn Val Asp Met Thr Ile
        435                 440                 445

Val Gln Glu Gly Ser Phe Val Ser Phe Glu His Gln Gln Pro Leu Glu
450                 455                 460

Asp Arg Met Ile Lys Phe Ser Phe Asn Met Thr Leu Pro Gly Asn Phe
465                 470                 475                 480

Gly Leu Ile Thr Ser Glu Glu Val Lys Ser Phe Phe Arg Met Gly Ala
                485                 490                 495

Lys Leu Ala Ala Gln Pro Asp Ile Met Asn Cys Pro Ile Phe Lys Lys
            500                 505                 510

Gly Pro Ala Ser Ile Arg His Leu Val Pro Val Gly Glu Ile Pro Pro
        515                 520                 525

Pro Lys Glu Met Lys His Lys Arg Gln Pro Leu Tyr Met Arg Ala Glu
530                 535                 540

Pro Asp Glu Ile Gln Asp Asn Pro Glu Glu Leu Asp His Trp Phe Glu
545                 550                 555                 560

Glu Glu Ala Pro Arg Lys Lys Gln Lys Thr Lys Asn Thr Ala Thr
                565                 570                 575

Lys Asn Pro Ala Glu Thr Val Glu Ile Ile Thr Glu Thr Glu Phe Ile
            580                 585                 590

Pro Ala Pro Gly Lys
            595
```